United States Patent
Kamel et al.

(10) Patent No.: US 9,549,834 B2
(45) Date of Patent: Jan. 24, 2017

(54) EMERGENCY VESSEL REPAIR PROSTHESIS DEPLOYMENT SYSTEM

(71) Applicant: Cook Medical Technologies LLC, Bloomington, IN (US)

(72) Inventors: Amro Kamel, Bloomington, IN (US); Eugene E. Skelton, Dublin (IE); Darren P. Corner, Derbyshire (GB); Shawn Nichols, Bloominton, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/689,358

(22) Filed: Apr. 17, 2015

(65) Prior Publication Data

US 2015/0216689 A1    Aug. 6, 2015

Related U.S. Application Data

(62) Division of application No. 13/589,571, filed on Aug. 20, 2012, now Pat. No. 9,011,514.

(Continued)

(51) Int. Cl.
*A61F 2/95* (2013.01)
*A61B 17/00* (2006.01)
(Continued)

(52) U.S. Cl.
CPC .......... *A61F 2/95* (2013.01); *A61B 17/00234* (2013.01); *A61F 2/064* (2013.01);
(Continued)

(58) Field of Classification Search
CPC ............ A61F 2/95; A61F 2/962; A61F 2/966; A61F 2/97; A61F 2/064; A61F 2002/9505; A61F 2002/9522; A61F 2002/9534; A61F 2002/9583; A61F 2002/9665; A61F 2/954; A61B 17/00234; A61B 2017/1132; A61B 2017/1107

See application file for complete search history.

(56) References Cited

U.S. PATENT DOCUMENTS

| | | |
|---|---|---|
| 4,038,987 A | 8/1977 | Komiya |
| 4,306,562 A | 12/1981 | Osborne |

(Continued)

FOREIGN PATENT DOCUMENTS

| | | |
|---|---|---|
| EP | 0775470 A1 | 5/1997 |
| FR | 2885794 A1 | 11/2006 |
| WO | WO 2007/084762 A2 | 7/2007 |

*Primary Examiner* — Jocelin Tanner
(74) *Attorney, Agent, or Firm* — Brinks Gilson & Lione

(57) ABSTRACT

A deployment device to deploy a prosthesis for interconnecting vessel portions of a body vessel is described herein. The device includes a support frame and an actuation member coupled to the support frame. The actuation member is movable between a first and a second position. A retaining member is movable between a closed and a open position. In the closed position, the retaining member forms a chamber to retain a length of a prosthesis in a compressed configuration. In the open position, the retaining member is positioned to allow the prosthesis to move to an expanded configuration. Movement of the actuation member to the second position causes movement of the retaining member to the open position. One or more retractable cuffs can be positioned over the ends of the prosthesis for selectively retaining the corresponding prosthesis ends in the compressed configuration.

18 Claims, 26 Drawing Sheets

Related U.S. Application Data

(60) Provisional application No. 61/526,048, filed on Aug. 22, 2011.

(51) Int. Cl.
*A61F 2/06* (2013.01)
*A61B 17/11* (2006.01)

(52) U.S. Cl.
CPC ............ *A61B 2017/1107* (2013.01); *A61B 2017/1132* (2013.01); *A61F 2002/9505* (2013.01); *A61F 2002/9522* (2013.01)

(56) References Cited

U.S. PATENT DOCUMENTS

| | | | |
|---|---|---|---|
| 4,581,025 A | 4/1986 | Timmermans | |
| 4,715,377 A | 12/1987 | Arroyo | |
| 4,982,727 A | 1/1991 | Sato | |
| 5,320,602 A | 6/1994 | Karpiel | |
| 5,380,304 A | 1/1995 | Parker | |
| 5,591,226 A | 1/1997 | Trerotola et al. | |
| 5,618,307 A | 4/1997 | Donlon et al. | |
| 5,624,454 A | 4/1997 | Palti et al. | |
| 5,647,857 A | 7/1997 | Anderson et al. | |
| 6,206,931 B1 | 3/2001 | Cook et al. | |
| 6,241,758 B1 | 6/2001 | Cox | |
| 6,346,118 B1 | 2/2002 | Baker et al. | |
| 6,432,127 B1 | 8/2002 | Kim et al. | |
| 6,447,540 B1 | 9/2002 | Fontaine et al. | |
| 6,562,049 B1 | 5/2003 | Norlander et al. | |
| 6,676,666 B2 | 1/2004 | Vrba et al. | |
| 6,692,464 B2 | 2/2004 | Graf | |
| 6,712,791 B2 | 3/2004 | Lui et al. | |
| 6,827,731 B2 | 12/2004 | Armstrong et al. | |
| 6,939,337 B2 | 9/2005 | Parker et al. | |
| 7,244,444 B2 | 7/2007 | Bates | |
| 7,413,573 B2 | 8/2008 | Hartley et al. | |
| 7,691,140 B2 | 4/2010 | Bates et al. | |
| 2002/0099431 A1 | 7/2002 | Armstrong et al. | |
| 2004/0249433 A1 | 12/2004 | Freitag | |
| 2005/0277959 A1 | 12/2005 | Cosgrove et al. | |
| 2006/0089627 A1* | 4/2006 | Burnett | A61B 17/12099 606/1 |
| 2007/0027526 A1 | 2/2007 | Demetriades et al. | |
| 2007/0055339 A1* | 3/2007 | George | A61F 2/95 623/1.11 |
| 2007/0198077 A1 | 8/2007 | Cully et al. | |
| 2007/0225659 A1 | 9/2007 | Melsheimer | |
| 2008/0221659 A1 | 9/2008 | Hartley et al. | |
| 2008/0255580 A1* | 10/2008 | Hoffman | A61F 2/95 606/108 |
| 2008/0288042 A1 | 11/2008 | Purdy et al. | |
| 2009/0076529 A1 | 3/2009 | Ganti | |
| 2009/0112237 A1 | 4/2009 | Paul, Jr. et al. | |
| 2009/0319022 A1 | 12/2009 | Hartley et al. | |
| 2010/0100167 A1* | 4/2010 | Bortlein | A61F 2/2436 623/1.11 |
| 2011/0301685 A1* | 12/2011 | Kao | A61F 2/95 623/1.11 |
| 2012/0035706 A1 | 2/2012 | Paul, Jr. et al. | |
| 2012/0035708 A1 | 2/2012 | Paul, Jr. et al. | |
| 2012/0123511 A1* | 5/2012 | Brown | A61F 2/064 623/1.11 |
| 2012/0165915 A1 | 6/2012 | Melsheimer et al. | |

\* cited by examiner

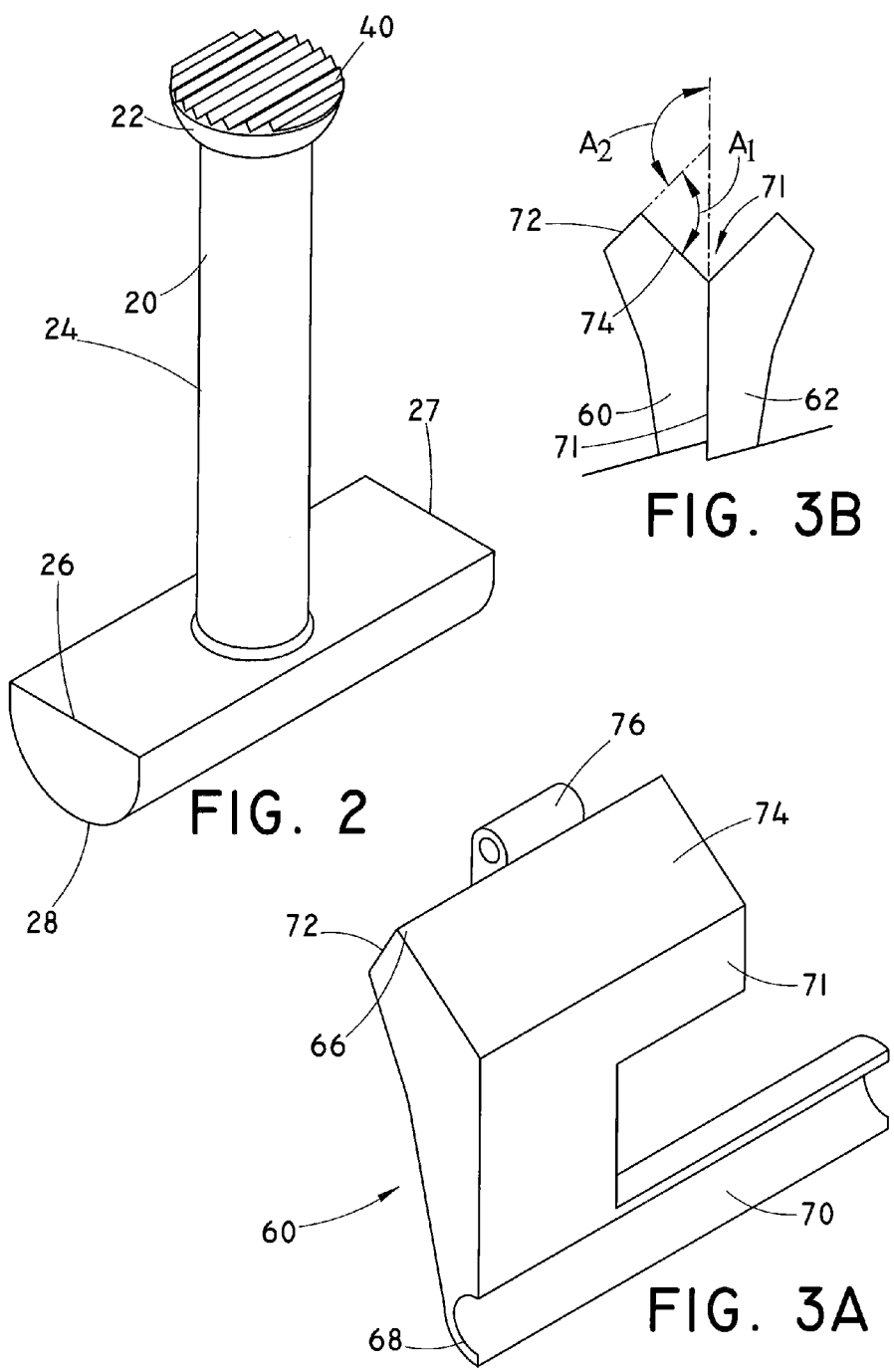

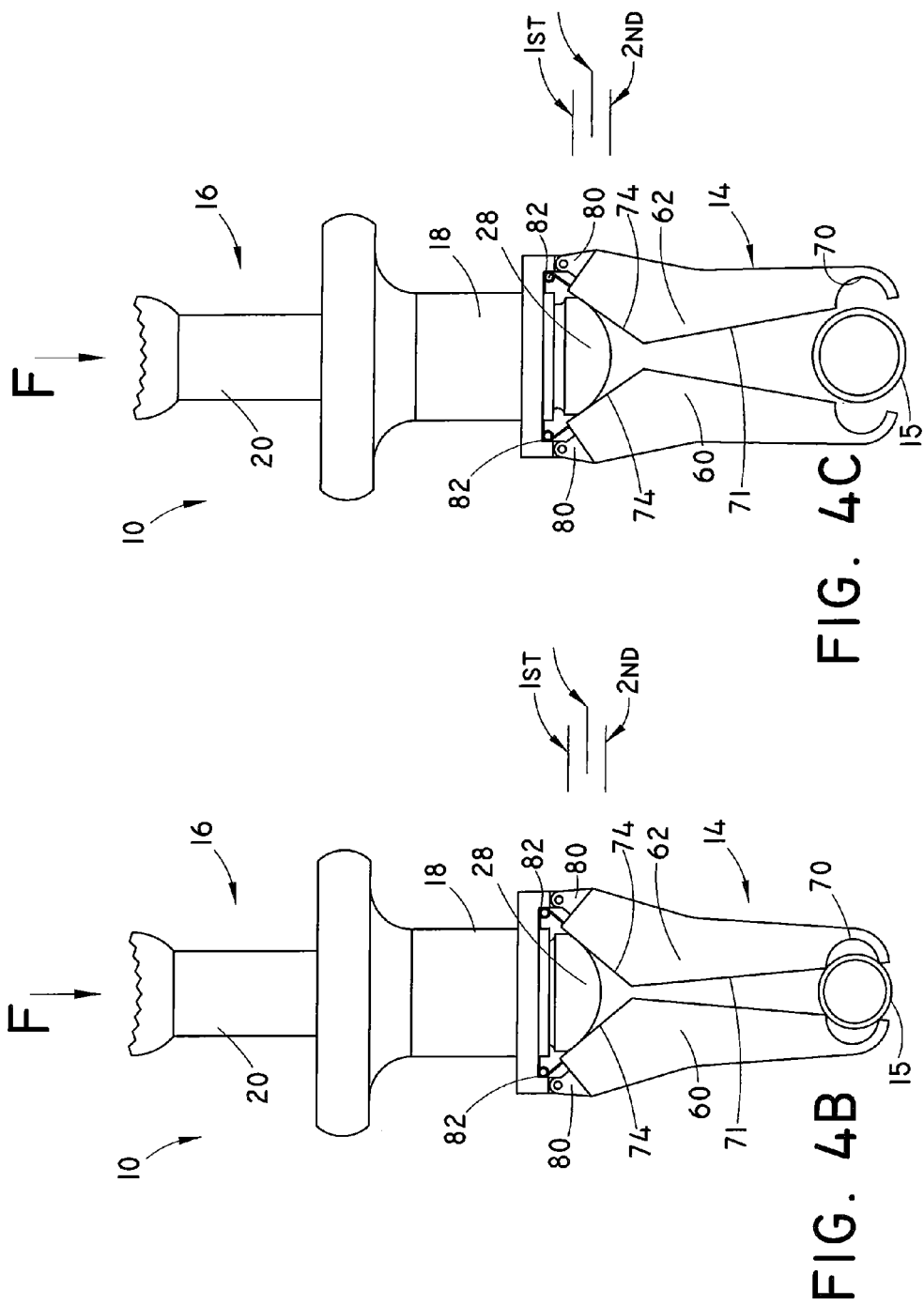

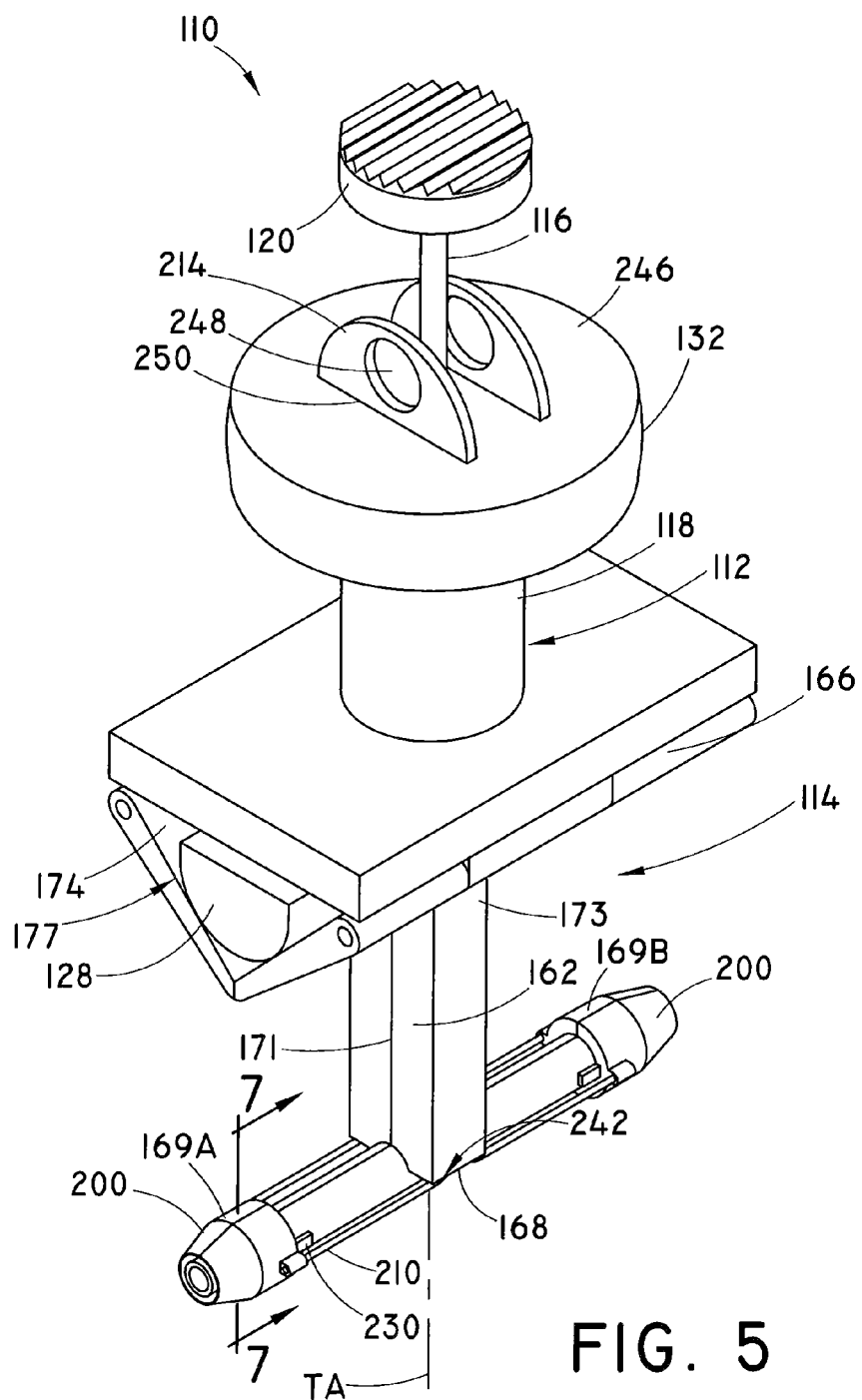

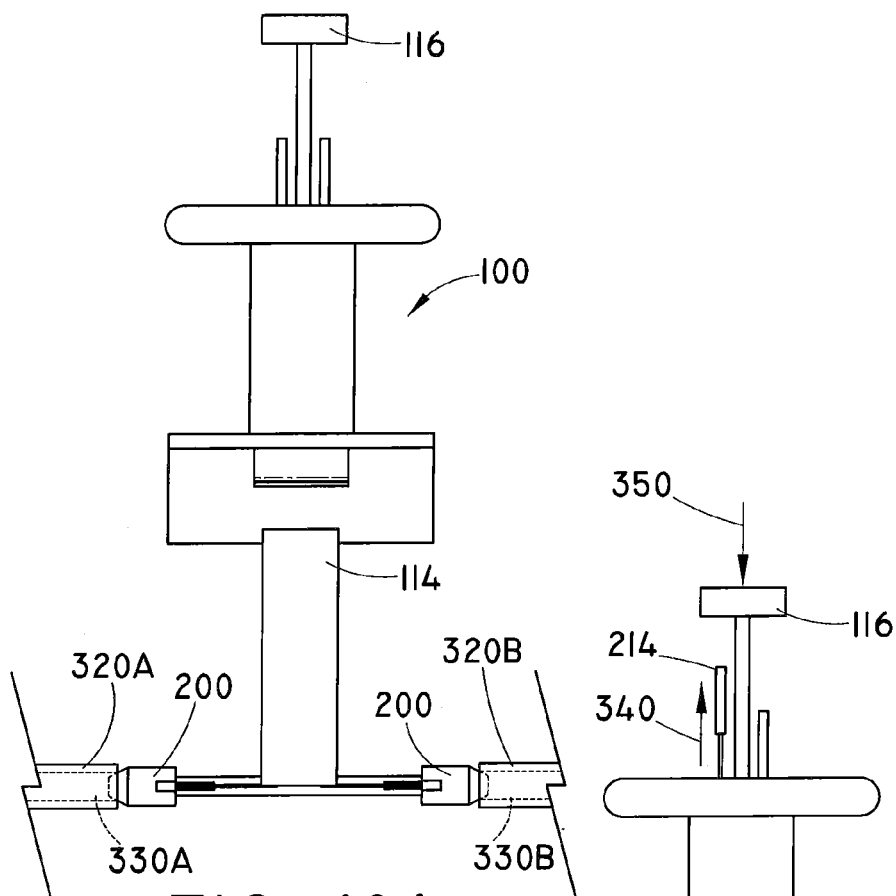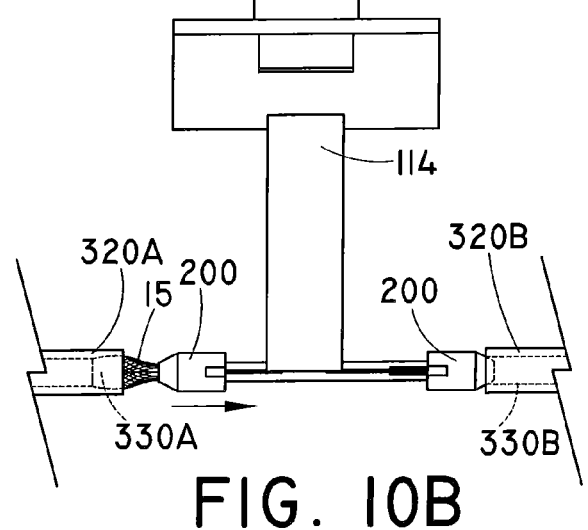
FIG. 10A
FIG. 10B

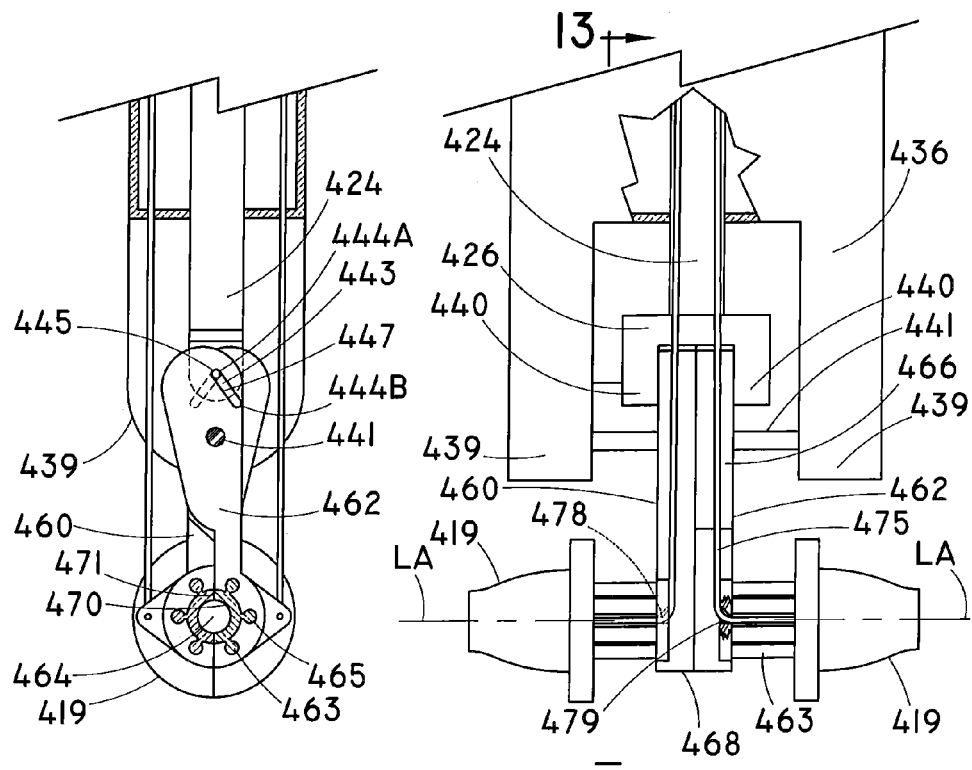
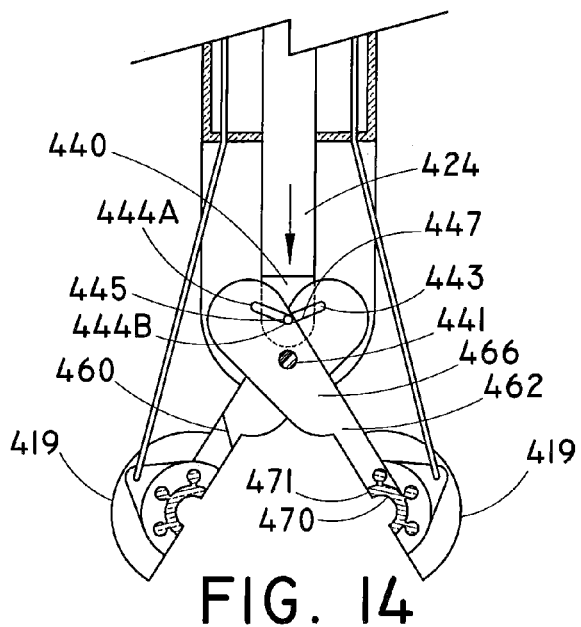
FIG. 13
FIG. 12
FIG. 14

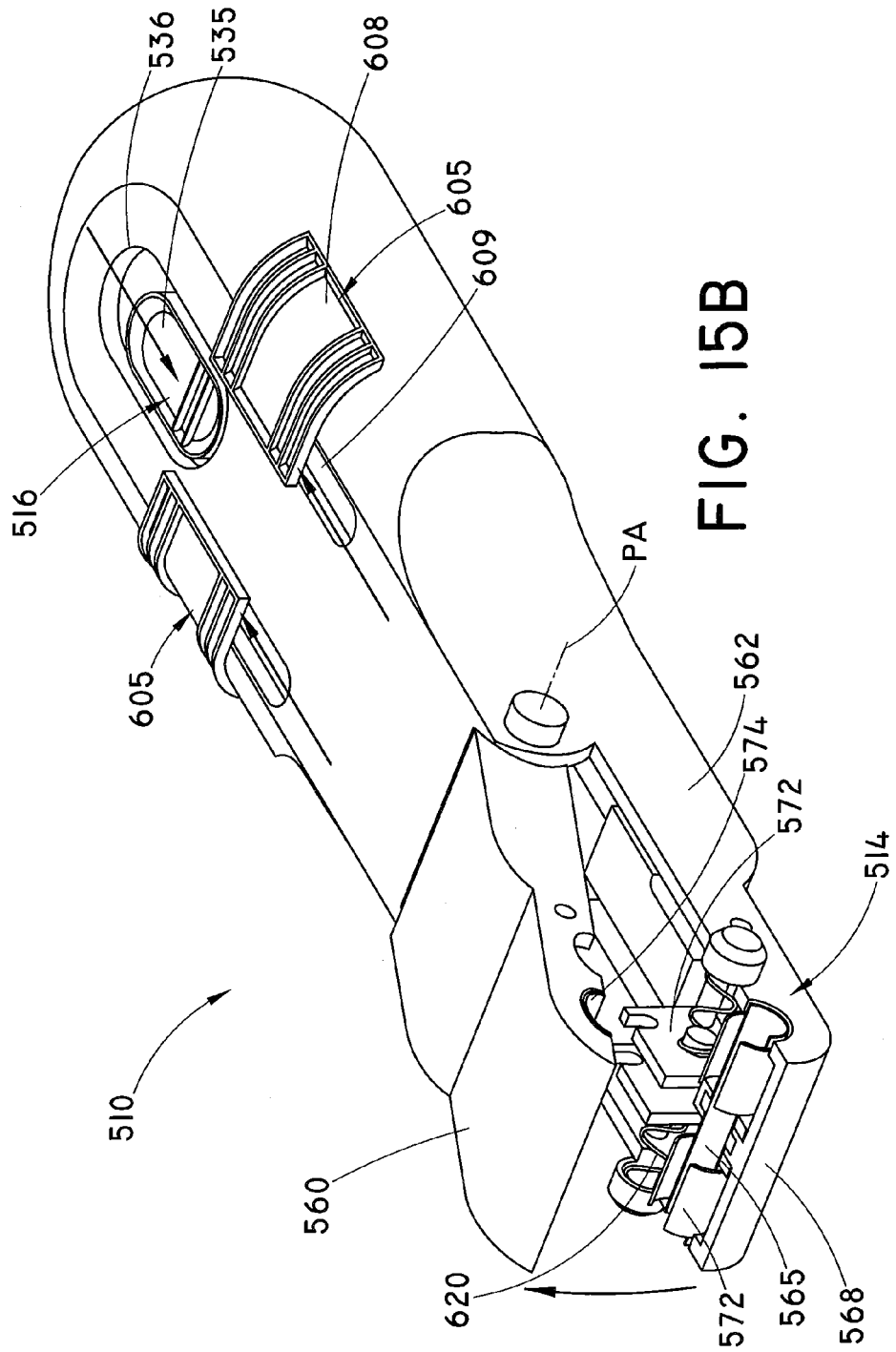

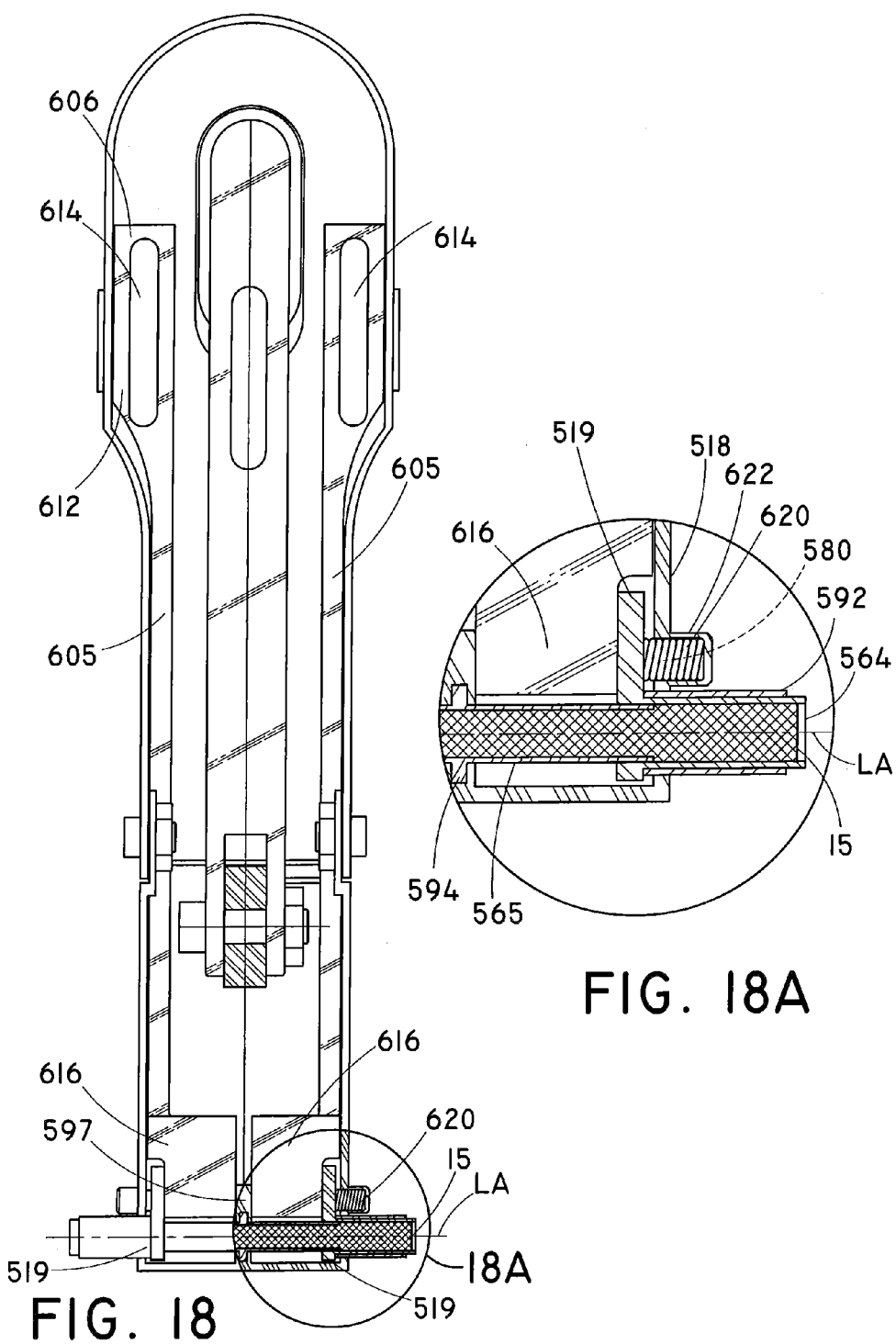

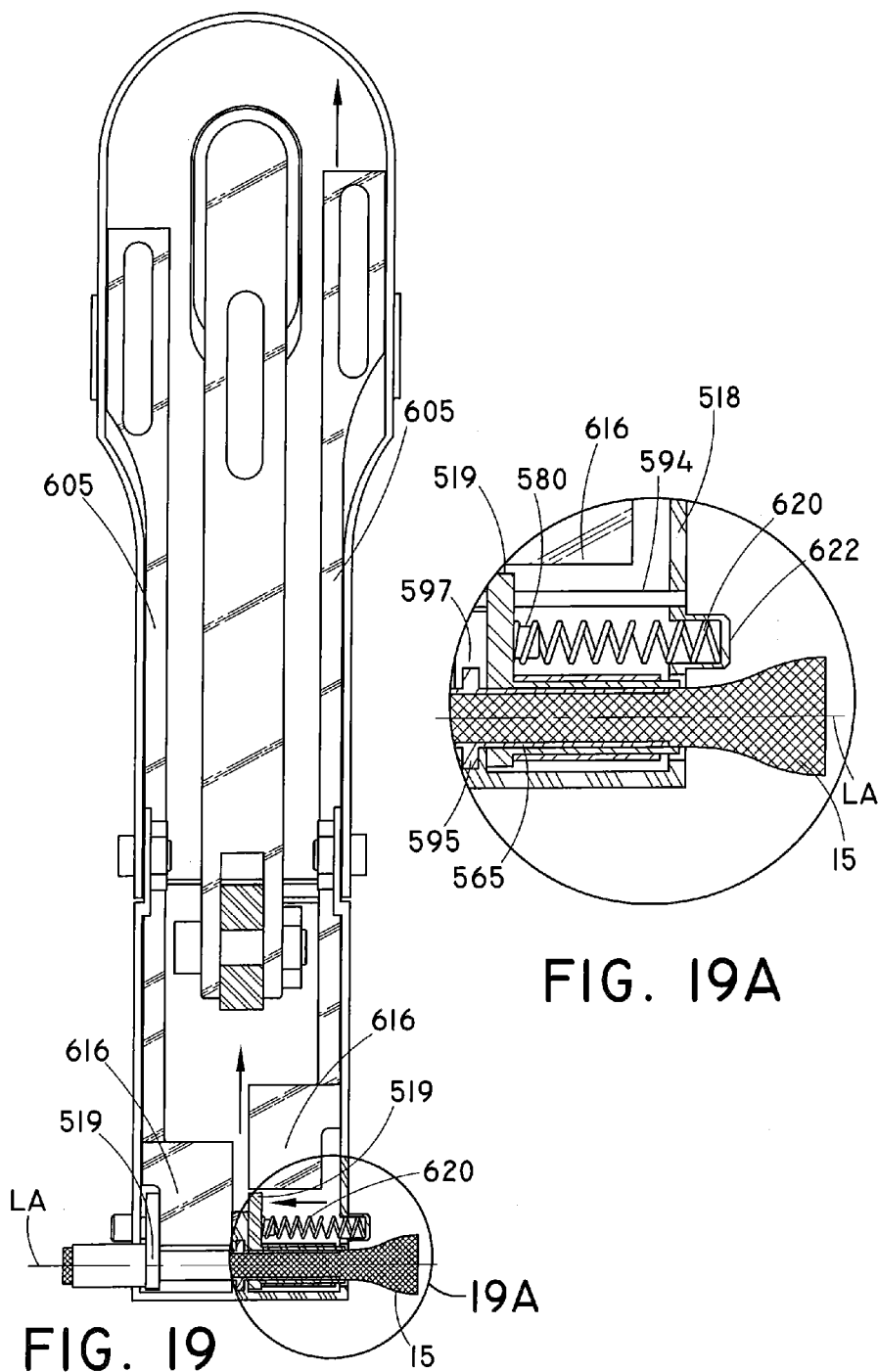

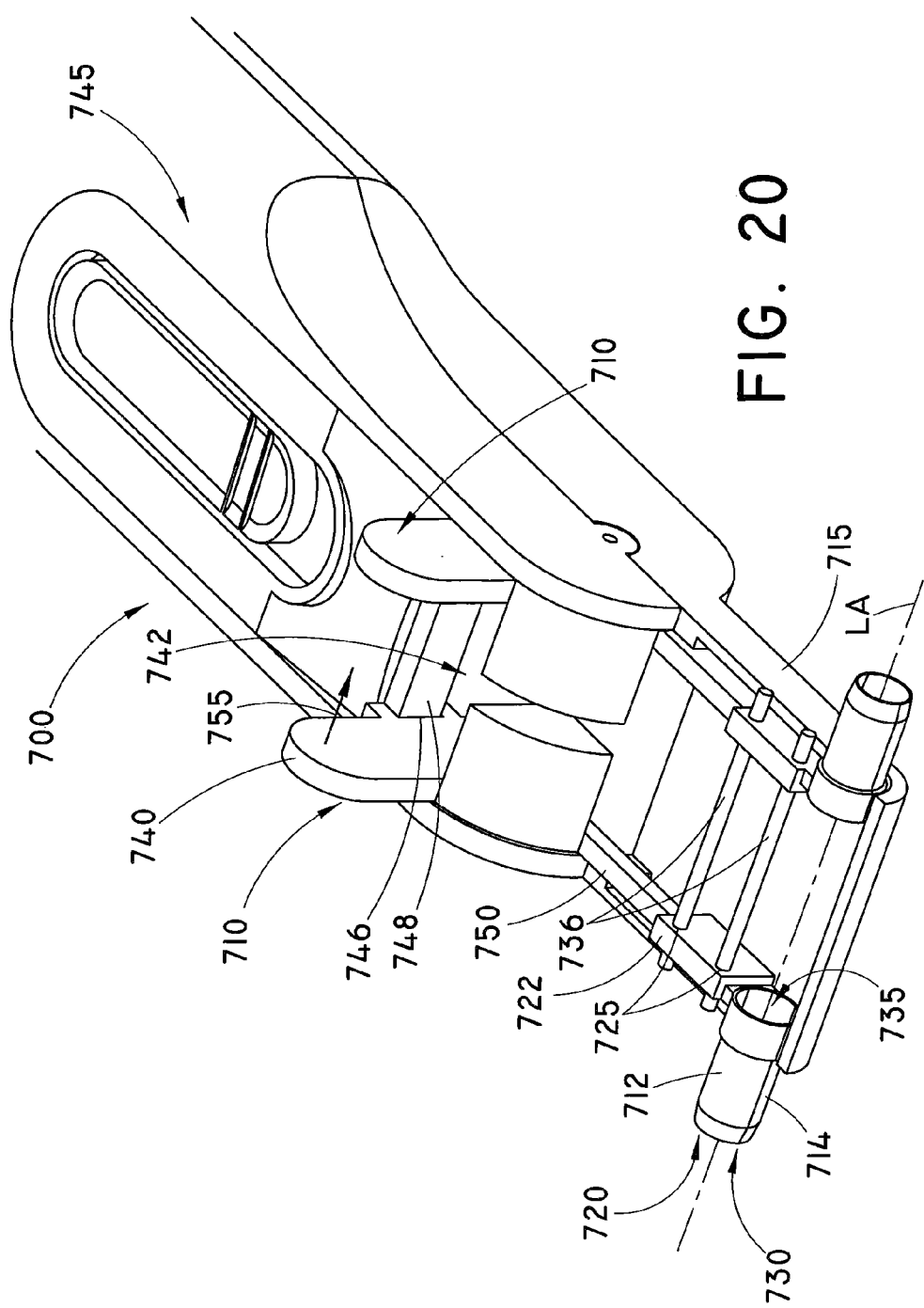

EMERGENCY VESSEL REPAIR PROSTHESIS DEPLOYMENT SYSTEM

RELATED APPLICATION

This application is a divisional application of U.S. Nonprovisional application Ser. No. 13/589,571, filed on Aug. 20, 2012, which claimed priority from U.S. Provisional U.S. Patent Application Ser. No. 61/526,048, filed Aug. 22, 2011, the entirety of which are each hereby incorporated by reference.

BACKGROUND

The present disclosure relates generally to medical devices. More particularly, it relates to deployment systems used for repairing damaged body vessels and gaining hemostasis during emergency medical procedures.

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include the clamping of the vessel with a hemostat, the use of a balloon tamponade, the ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. With respect to ligation, ligation of the damaged blood vessel may result in muscle necrosis, loss of muscle function, or a potential limb loss or death.

Due to the nature of the body vessel injury that may be encountered, the insertion of shunts or ligation of a blood vessel, for example, often requires that such treatments be rapidly performed at great speed, and with a high degree of physician skill. Such treatments may occupy an undue amount of time and attention of the trauma physician at a time when other pressing issues regarding the patient's treatment require immediate attention. In addition, the level of particularized skill required to address a vascular trauma may exceed that possessed by the typical trauma physician. In particular, traumatic episodes to the vessel may require the skills of a physician specially trained to address the particular vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures, and the blood flow is more quickly restored and damage caused by lack of blood flow is minimized.

Trauma physicians generally find it difficult to manipulate a prosthesis for insertion into a body vessel that has been traumatically injured. For example, one difficulty arises from the trauma physician trying to limit the size of the opening created for gaining access to the injured vessel so that such opening requiring healing is as small as possible. Another difficulty is that the injured vessel can be anywhere in the body, having different surrounding environments of bone structure, muscle tissue, blood vessels, and the like, which makes such obstructions difficult to predict in every situation and leaves the trauma physician working with an even further limited access opening. Another potential consideration is the amount of body vessel removed during a transection. The goal would be to remove a portion of the body vessel as small as possible. Yet, a small portion removed from the vessel leaves such a small space between the two vessel portions, thereby making it difficult to introduce the prosthesis between the two vessel portions.

Thus, what is needed is a deployment device for delivering a prosthesis for use in repair of an injured body vessel, such as an artery or a vein, (and in particular a transected vessel) during emergency surgery. It would be desirable if such deployment device was easy for a trauma physician to use, and can rapidly introduce a prosthesis into two vessel portions of a transected vessel, thereby providing a conduit for blood within the injured body vessel.

SUMMARY

Accordingly, various examples of deployment devices are provided herein to address at least some of the shortcomings of the prior art. The deployment device can be used to connect a first vessel portion and a second vessel portion of a body vessel such as, e.g., for open surgical repair of a body vessel. In one example, the device can include a support frame and an actuation member coupled to the support frame. The actuation member is movable between a first and a second position. A retaining member, e.g., in the form of shells or clamps, is coupled to the actuation member and/or the support member. The retaining member is movable between a closed and an open position. In the closed position, the retaining member can form a chamber to retain a length of a prosthesis in a compressed configuration. In the open position, the retaining member is positioned to allow the prosthesis to move to an expanded configuration. Movement of the actuation member to the second position causes movement of the retaining member to the open position. The device may include one or more retractable cuffs at the prosthesis ends for selectively retaining the prosthesis ends in the compressed configuration.

In another example, the device can include a support frame and an actuation member coupled to the support frame. The actuation member is movable relative to the support frame between a first position and a second position. A first shell and a second shell can be coupled to the support frame. The shells are movable relative to one another between a closed position and an open position. In the closed position, the first shell and the second shell are positioned in close proximity to form a retaining chamber to retain at least an intermediate segment of a prosthesis in a radially compressed configuration. In the open position, the first shell and the second shell are positioned away from one another to allow the segment of the prosthesis to move to a radially expanded configuration. The device can include retractable ends, such as a first and a second retractable cuff, coupled to the first and second shells to selectively retain the first and second outer ends of the prosthesis in the radially compressed configuration. Movement of the actuation member from the first position to the second position causes the first and second shells to move from the closed position to the open position.

In yet another example, a method of treating a body vessel is described herein. The method can include introducing a deployment system having a prosthesis within a body. The system can include a support frame and an actuation member coupled to the support frame. The actuation member is movable relative to the support frame along a first axis between a first position and a second position. A retaining member is coupled to the support frame. The retaining member is movable between a closed position and an open position. In the closed position, the retaining member can form a retaining chamber to retain at least an intermediate length of the prosthesis in the radially compressed configuration. The deployment system is introduced with the actuation member in the first position and the retaining member in the closed position. The first outer end of the prosthesis can be introduced into a first vessel portion. The second outer end of the prosthesis can be introduced into a second vessel portion. The actuation member can be moved from the first position to the second position to actuate the retaining member to move to an open position. This movement can allow at least the intermediate length of the prosthesis to move to a radially expanded configuration in order for the prosthesis to connect the first and second vessel portions together. Retractable ends can be moved inward to a position to permit expansion of the outer ends of the prosthesis prior to the moving the actuation member.

BRIEF DESCRIPTIONS OF THE DRAWINGS

FIG. 2 is a perspective view of an actuation member of the deployment device of FIG. 1.

FIG. 3A is a perspective view of a retaining member of the deployment device of FIG. 1.

FIG. 3B is a partial side view of the retaining member in a closed position.

FIGS. 4A-4C are side views depicting operation of the deployment device of FIG. 1.

FIG. 5 is a perspective view of another example of a deployment device pre-loaded with a prosthesis.

FIGS. 10A-10C illustrate a method of connecting body vessel portions with the deployment device of FIG. 5 to treat a body vessel.

FIG. 12 is a front view of a distal end of the deployment device of FIG. 11.

FIG. 13 is a cross sectional view of a distal end of the deployment device taken along lines 12-12, depicting a retaining member in a closed position.

FIG. 14 is a cross sectional view of a distal end of the deployment device of FIG. 13, depicting a retaining member in an open position.

FIG. 15B is a perspective view of the deployment device of FIG. 15A, with the retaining member in the open position.

FIGS. 18-19 illustrate movement of a release member and a retractable cuff.

FIGS. 18A-19A are magnified views of a portion of the device shown in FIGS. 18-19, respectively, to depict the movement between the release member and the retractable cuff.

FIG. 20 is a partial perspective view of another example of a deployment device with another embodiment of retractable cuffs.

Figure 21:
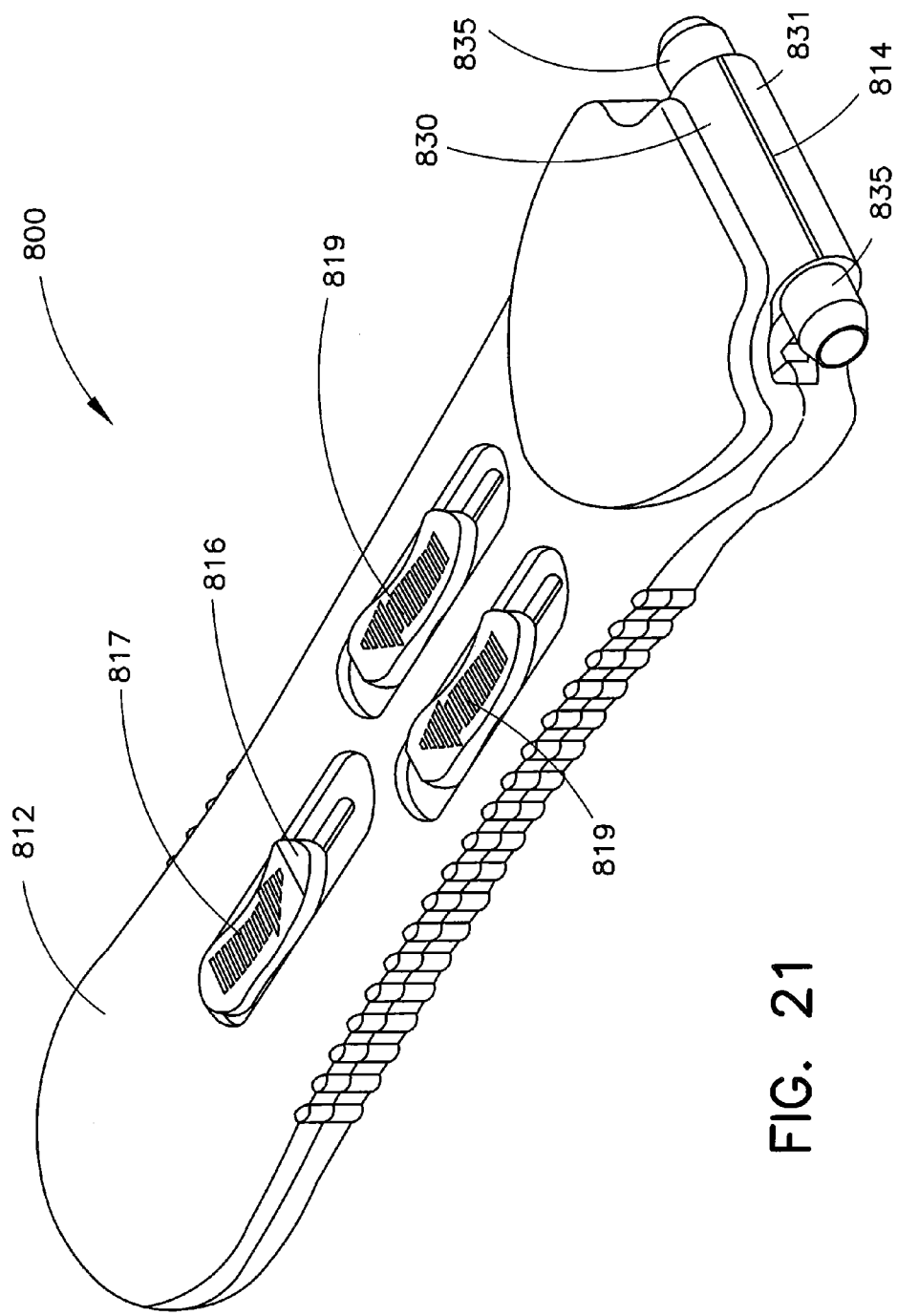

FIG. 21 a perspective view of another example of a deployment device, with a retaining member in the closed position.

Figure 22:
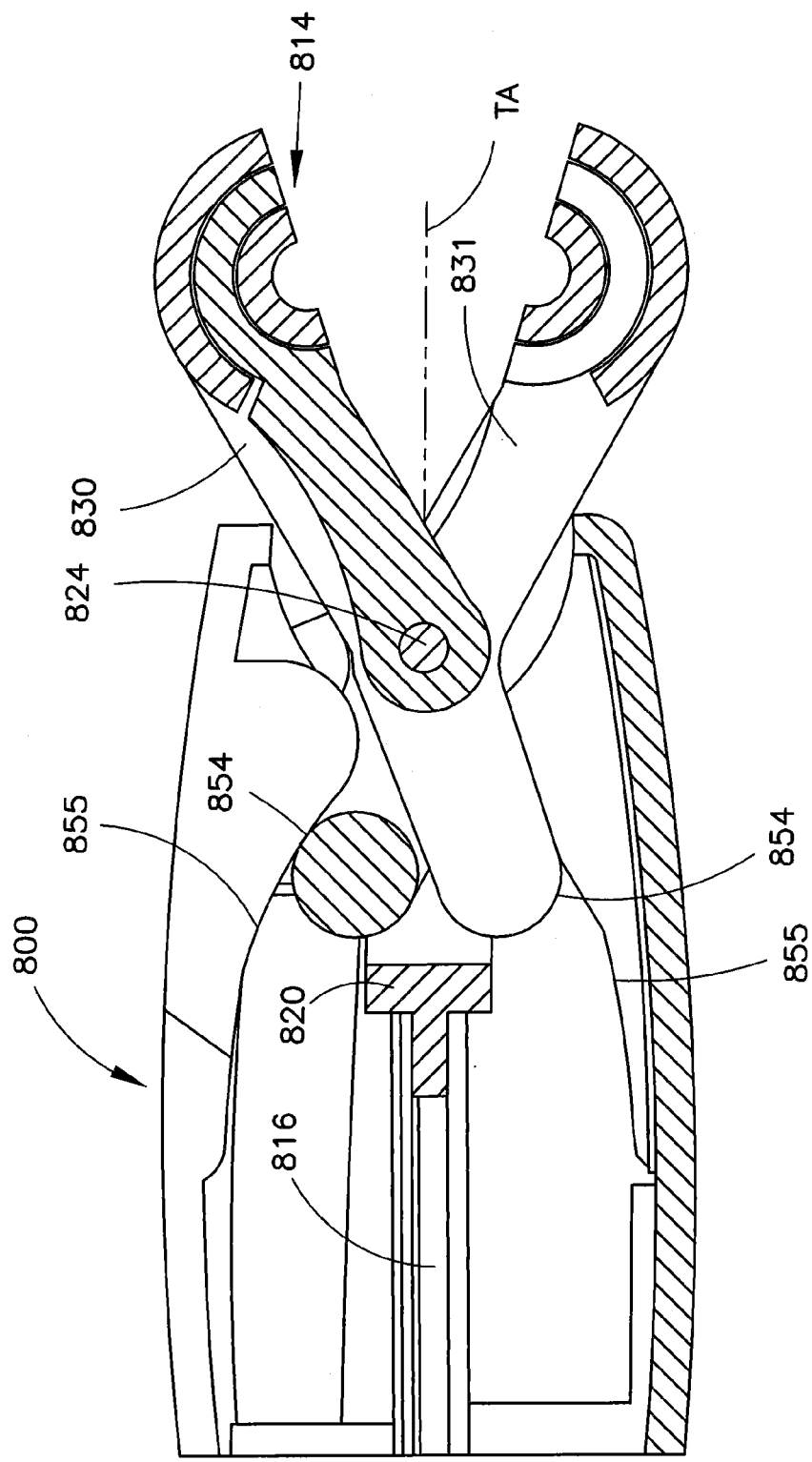

FIG. 22 is a cross-sectional view of a distal end of the deployment device of FIG. 21, with the retaining member in the open position.

Figure 23A:
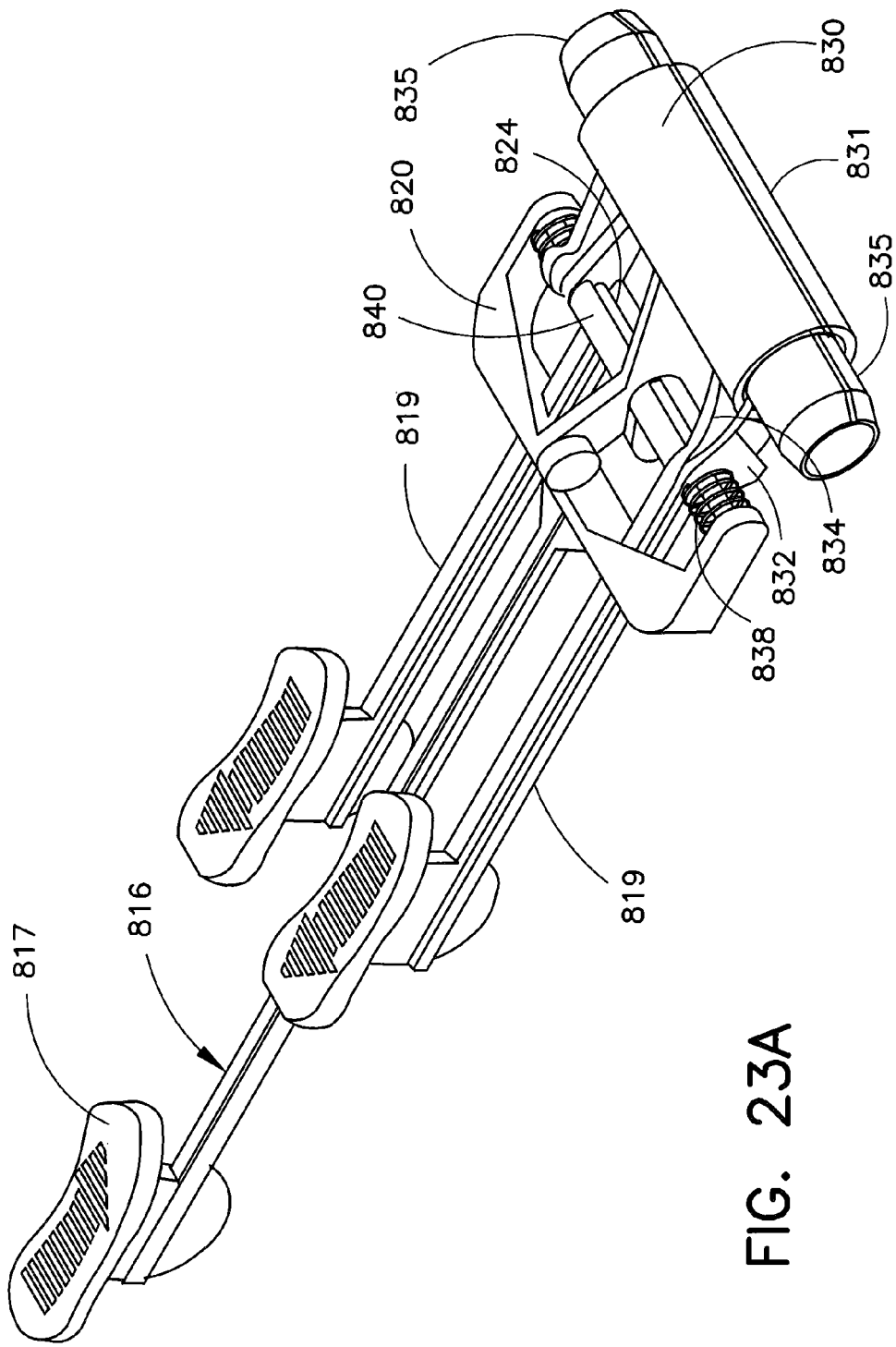
Figure 23B:
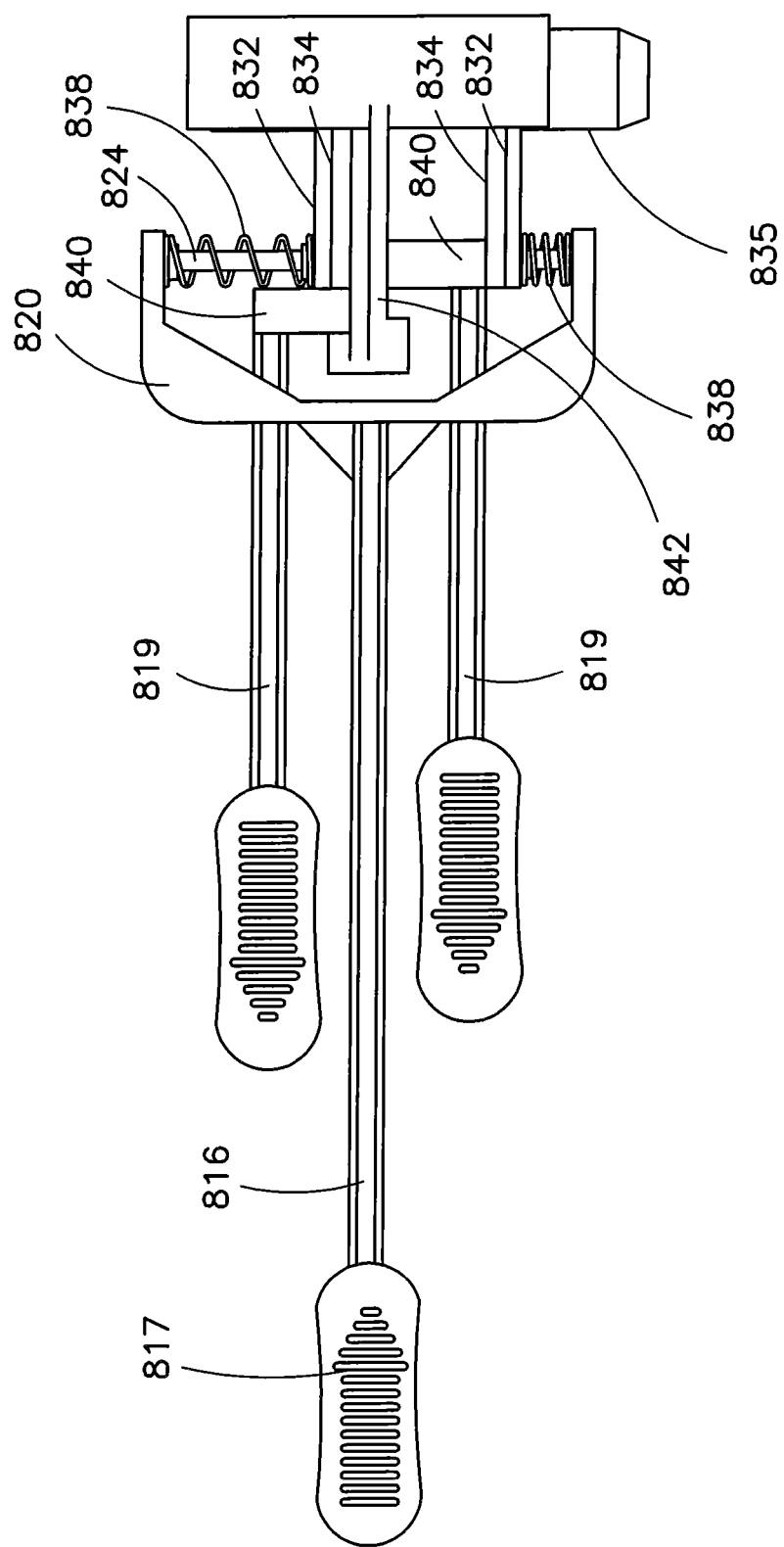

FIGS. 23A-B illustrate examples of an actuation member and a release member provided with the deployment device of FIG. 21.

Figure 24:
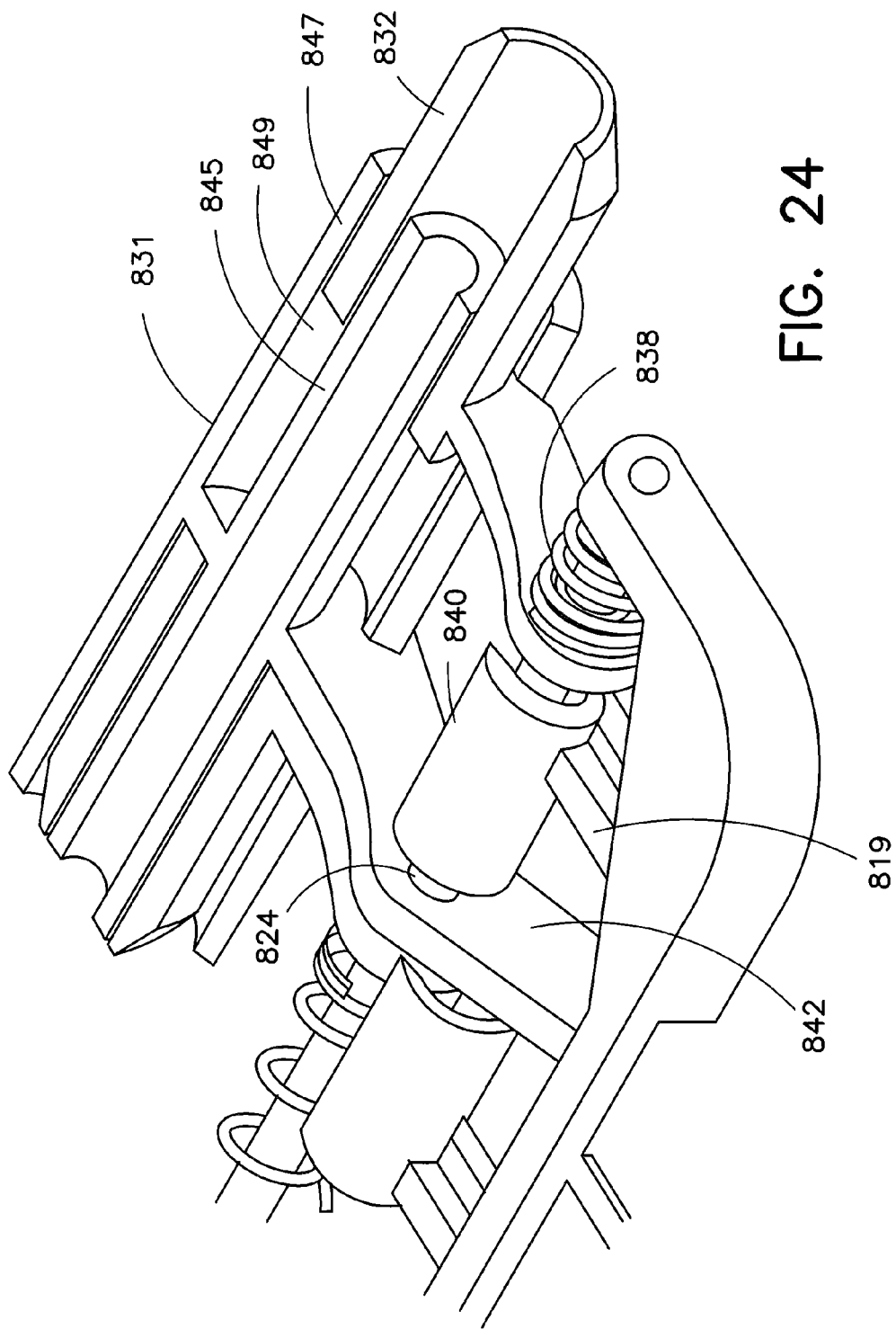
Figure 25:
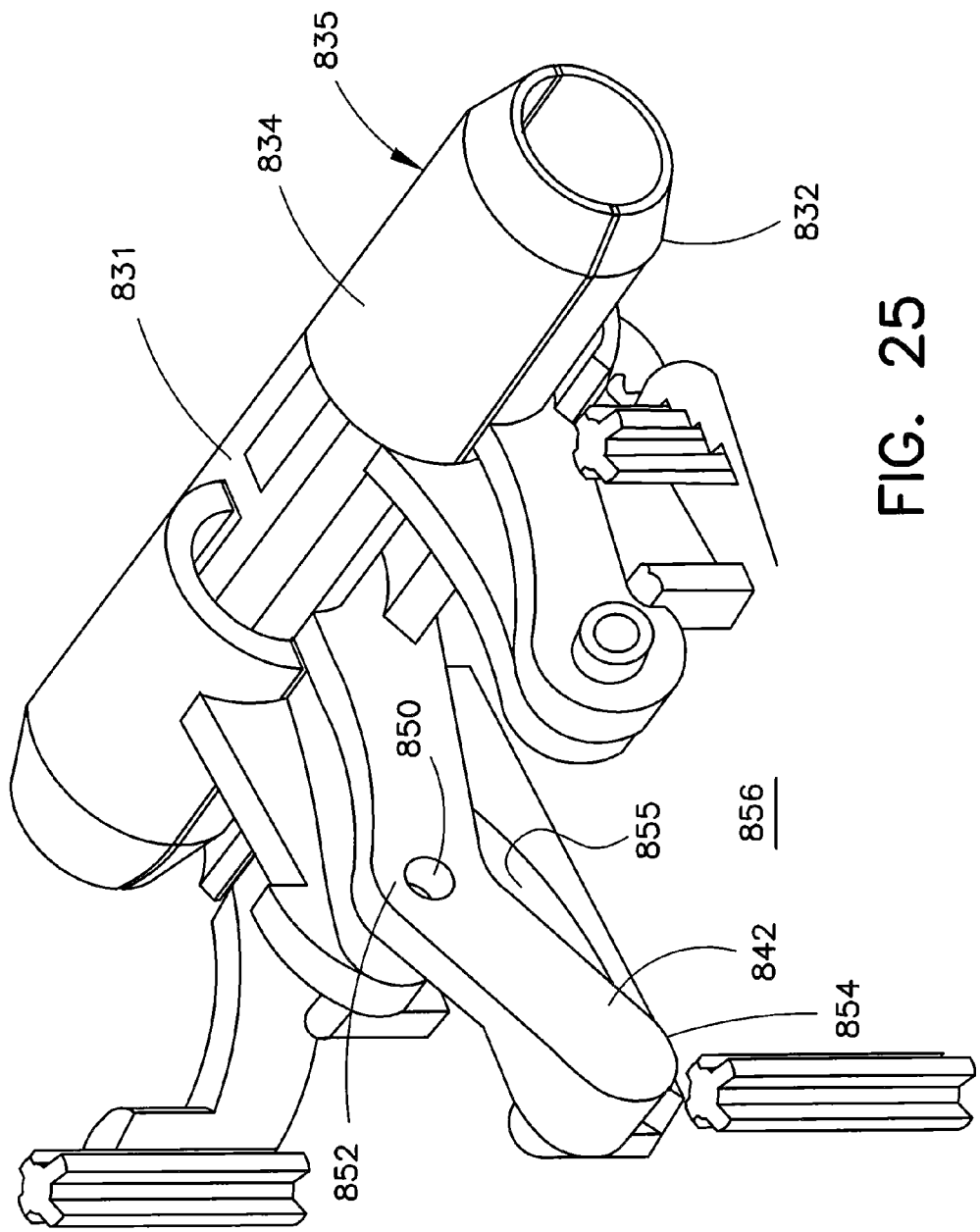

FIGS. 24-25 are perspective views of a distal end of the deployment device of FIG. 21, depicting one arrangement of a shell and a cuff.

DETAILED DESCRIPTION OF THE DRAWINGS AND THE PRESENTLY PREFERRED EMBODIMENTS

For the purposes of promoting an understanding of the principles of the present disclosure, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Throughout the specification, when referring to a medical device, or a portion of a medical device, the terms "distal" and "distally" shall denote a position, direction, or orientation that is generally towards, or in the direction of, the patient when the device is in use. The terms "proximal" and "proximally" shall denote a position, direction, or orientation that is generally away from the patient, or closer to the operator, during use of the device. It is understood that like-referenced numerals are used throughout the Figures to designate similar components.

The deployment devices described herein can be useful for repair of body structures or vessels that define lumens, ducts, or passageways, with the term "body vessel" used in the specification to describe theses structures in general, during emergency open surgical repair. In one example, the prosthesis can be particularly useful for repair of a lacerated or transected artery or vein during emergency open surgery, and particularly, to obtain hemostasis or fluid stability while maintaining blood perfusion or fluid flow. While some prosthetic devices are only implanted temporarily for treatment, the prosthesis can be implanted permanently thereby obviating the need for further surgical intervention and repair.

Such devices are typically inserted through a trauma pathway that is formed in the body to gain access to the desired body vessel. The trauma pathway can be oblique, and on occasion perpendicular, to the desired body vessel, and is formed as small as possible to minimize any further damage to the body. To this end, the device can have an elongated body to minimize the cross-section relative to the cross-section of the trauma pathway and a length suitable to extend from the desired body vessel and out in a manner to allow the end user to operate the device. This can allow the end user to operate the device from the proximal end and deliver the prosthesis from the distal end. The device can include a support frame and an actuation member coupled to the support frame. The actuation member is movable to open and close a retaining member. In the closed position, the retaining member can form a chamber to retain at least a length of a prosthesis in a radially compressed configuration. In the open position, the retaining member is positioned to allow the prosthesis to move to a radially expanded configuration. The device may include retractable ends over the prosthesis ends for selectively retaining the outer ends in the compressed configuration. The various devices described herein have different arrangements of the actuation member, the retaining member, and the retractable ends, if employed.

Figure 1:
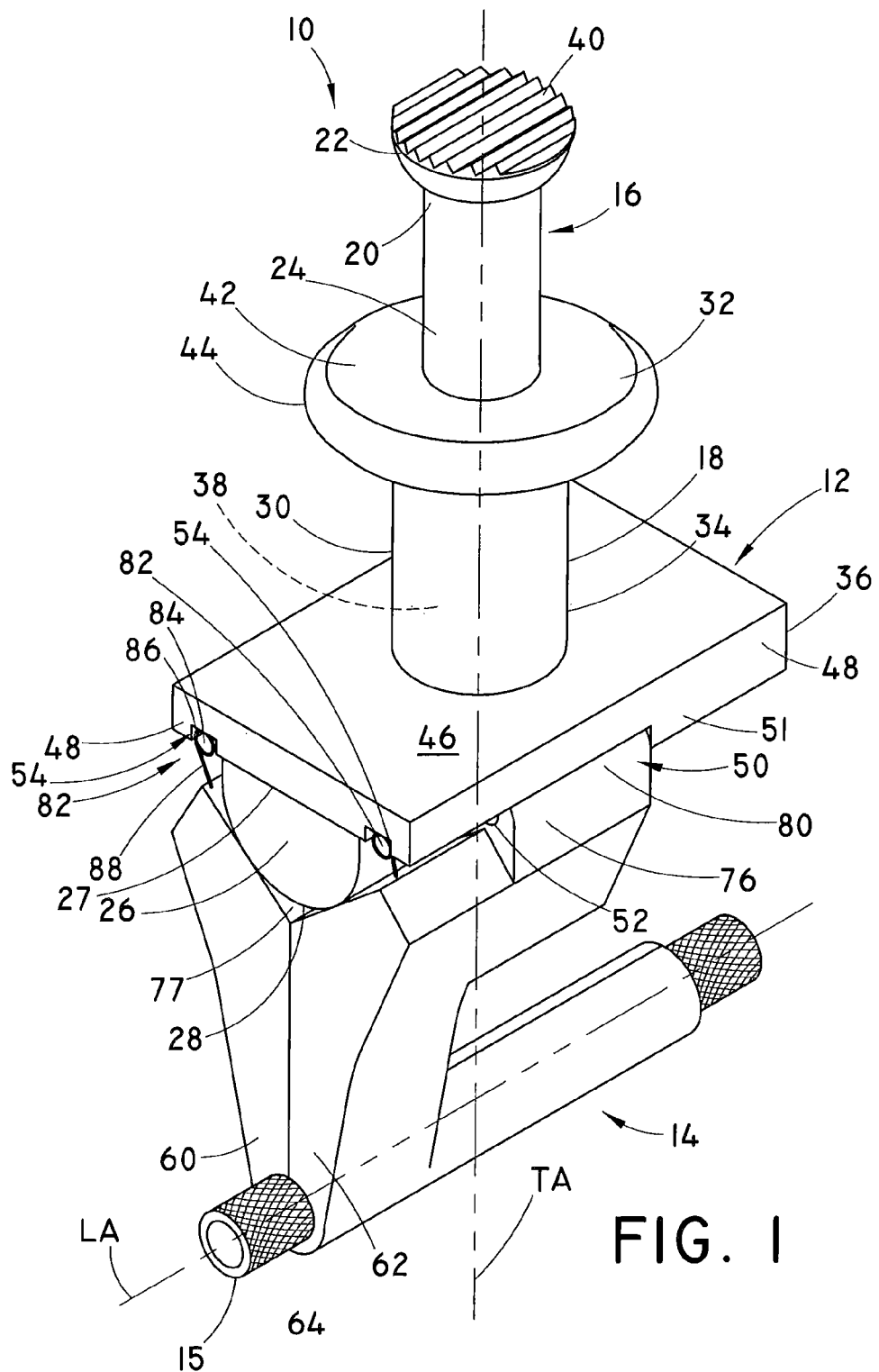
FIG. 1 is a perspective view of one example of a deployment device pre-loaded with a prosthesis.

FIG. 1 depicts one embodiment of a deployment device 10 having a handle portion 12 and a retaining member 14 that can retain a prosthesis 15 in a radially compressed configuration. The retaining member 14 is movable between a closed position, whereby at least a length of the prosthesis 15 is in the radially compressed configuration, and an open position, whereby the prosthesis 15 is permitted to move to a radially expanded configuration. The handle portion 12 can include an actuation member 16 coupled to a support frame 18. The actuation member 16 is configured to move relative to support frame 18 between a first position and a second position. When the actuation member 16 is in the first position, the retaining member 14 is in the closed position, and while in the second position, the retaining member 14 is in the open position.

In FIGS. 1-2, the actuation member 16 can include a plunger 20, which can have a first or proximal portion 22, an intermediate body 24, and a second or distal portion 26 coupled to one another. Support frame 18 can include a tubular body 30 that can have a proximal portion 32, an intermediate portion 34, and a distal portion 36 coupled to one another. Tubular body 30 can define a passageway 38 about a translational axis TA that can extend through the proximal and distal portions of the tubular body. The translational axis TA can be oblique or substantially perpendicular to a longitudinal axis LA of the prosthesis. The passageway 38 is sized to receive the elongated body 24 of the plunger so that the plunger is capable of being translated along the translational axis between a first position and a second position. The passageway 38 can include additional features, such as bearings and/or lubrication, to facilitate translation of the plunger.

The proximal portion 22 of the plunger 20 can extend proximally beyond the proximal portion 32 of the support frame 18, and the distal portion 26 of the plunger can extend distally beyond the distal portion 36 of the support frame. The proximal portion 22 of the plunger can be an enlarged member having a cross-section that is larger than the cross-section of the passageway 38. In FIG. 2, a proximal surface 40 of the proximal portion 22 can be planar and may be provided with surface irregularities, such as grooves, dimples, protrusions, or the like, formed in the surface 40 to improve grippability for the end user. The distal portion 26 can be elongated body that can generally extend oblique or substantially perpendicular to the translational axis TA, which may be substantially parallel to the longitudinal axis LA of the prosthesis. A distal end of the intermediate body 24 can be coupled to approximately the center portion of a proximal surface 27 of the distal portion 26. A distal surface 28 of the distal portion 26 may be contoured to have an increasingly smaller cross-sectional area toward the distal direction, such as rounded or wedged, to engage the shells 60, 62 of the retaining member 14, as will be explained. In one example, the distal portion 26 is a semi-cylindrical body.

The proximal portion 32 of the tubular body 30 of the support frame 18 can extend radially outward from the passageway 38 to define a gripping flange 42. The proximal portion 32 can be rounded and generally extend perpendicular to the translational axis TA. The cross-section of the gripping flange 42 may be larger than the cross-section of the proximal portion 22 of the plunger. The gripping flange 42 may have an outer edge 44 which may be rounded for facilitating handlability for the end user. The distal portion 36 of the tubular body 30 of the support frame 18 can be axially spaced from the proximal portion 32 of the support frame by the axial length of the intermediate body 34. The distal portion 36 can have a variety of geometric shapes. For example, the distal portion 36 can be a plate 46 with a rectangular shape having longer sides that are oriented along the same direction of the longitudinal axis LA of the prosthesis. The distal portion 36 can generally extend perpendicular to the translational axis TA. A pair of walls 48 may depend from a distal surface of the plate 46. The walls 48 can extend along the longer sides of the plate 46. Each of walls 48 may have a notch 50 formed therein to form a first hinge segment 51. A pin 52 can extend from an end portion of the first hinge segment 51 within the region of the notch 50 and along the general direction of the wall 48 to form a part of a hinge as will be explained. An inner groove 54 can be formed in the distal surface of the plate 46 along an inner side of the each of the walls 48.

The retaining member 14 can include a first shell 60 and a second shell 62 that together are configured to define a prosthesis retaining chamber 64 about the longitudinal axis LA when the retaining member is in the closed position, as shown in FIG. 1. FIG. 3A depicts an example of the first shell 60, with the second shell 62 being a mirror image of the first shell 60. Each of the shells can include a proximal portion 66 and a distal portion 68. The distal portion 68 can be shaped such that when the shells are in the closed position, the distal portion 68 forms a tubular chamber. In one example, a longitudinal recess 70 can be formed in a confronting surface 71 of the shell along the distal portion 68. The recess 70 can have a semi-circular cross-section, but other geometric cross-sections may be used so long as the recess is configured to receive at least about half of the prosthesis. Each recess 70 is configured so that when the shells are in the closed position the recesses together form the prosthesis retaining chamber 64 for retaining the prosthesis in the radially compressed configuration.

In FIG. 3A, the proximal portion 66 can be a bi-angled surface including an outer support surface 72 and an inner engaging surface 74 that is contiguous with the confronting surface 71. The outer support surface 72 can include a second hinge segment 76 configured to be coupled with the first hinge segment 51 of the support frame 18 with the pin 52 to form a hinged attachment 80 between the support frame 18 and the shells 60, 62, as shown in FIG. 1. The second hinge segment can be a cylindrical tubular member that is configured to receive the pin 52. As a result, the shells 60, 62 are capable of swinging inward and outward about the pivot axis formed by the hinged attachment 80 for movement of the retaining member 14 between the closed and open positions. The amount of material removed to form the notch 50 is sufficient to permit the hinged attachment 80 to be formed with the pin 52 and the second hinge segment 76. The confronting surface 71 can be a substantially planar surface. The confronting surfaces 71 of the first and second shells 60, 62 may engage one another when the shells are in the closed position to define a plane that is substantially coplanar with a plane defined by the translational and longitudinal axes TA, LA.

In FIG. 3B, the inner engaging surface 74 can be obliquely angled at a first angle A1 relative to the plane defined by the translational and longitudinal axes TA, LA, while the outer support surface 72 can be angled at a second angle A2. The first angle A1 can be configured so that each the inner engaging surface 74 of the shells 60, 62 in the closed position together form a retaining engaging surface 77 of the retaining member 14. The retaining engaging surface 77 can form a V-shape or a U-shape for slidable engagement with the distal portion 26 of the plunger 20. To this end, the distal surface 28 of the distal portion 26 of the plunger can be configured to slidably engage the converging or angled inner engaging surfaces 74 to allow for pivotable displacement of the shells 60, 62 outward about the respective pivot axes formed by the hinged attachments.

Figure 4A:
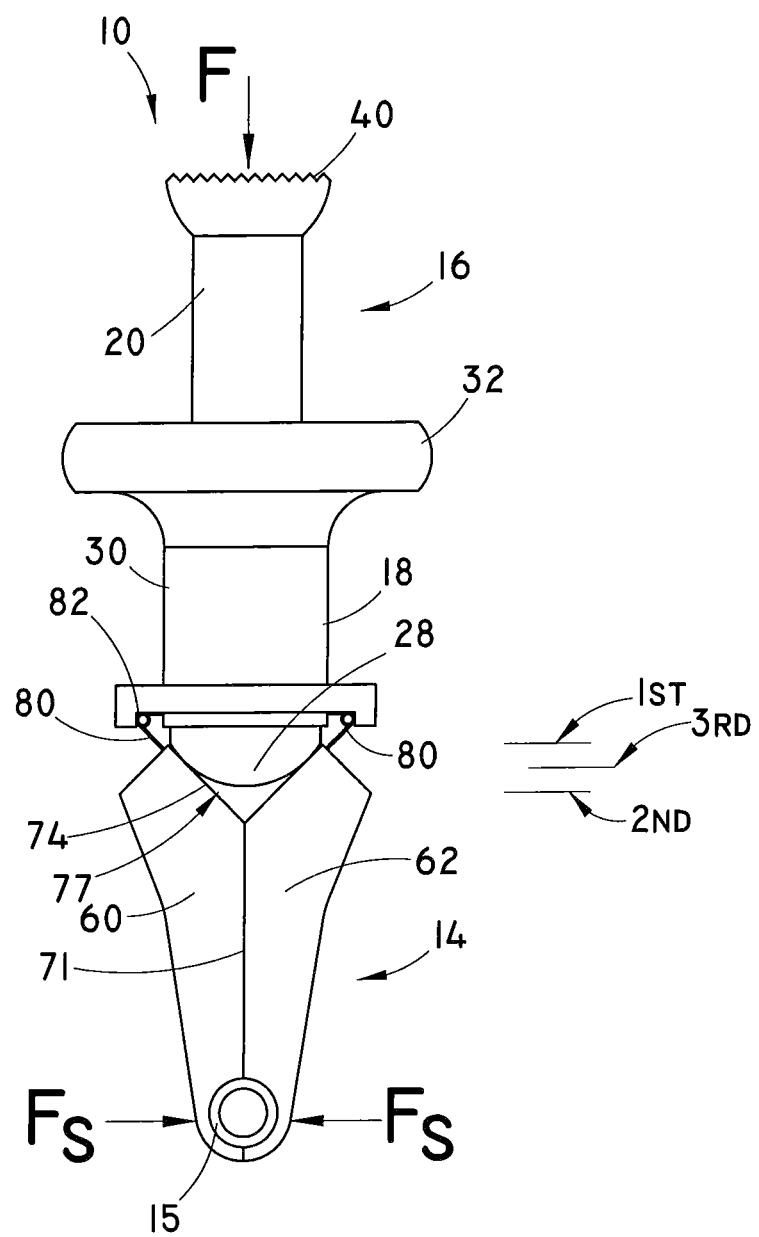

In FIG. 1, the device can include one or more biasing members to bias the shells 60, 62 in either the open or the closed position, but preferably in the closed position. The biasing member 82 can be coupled between the support frame 18 and each of the shells 60, 62. In one example, the biasing member 82 is a helical torsion spring having a coil 84 positioned within the inner groove 54 of the support frame 18, while a first leg 86 is fixed in a secure relationship with the support frame 18, and a second leg 88 is fixed in a secure relationship with each of the shells 60, 62. The outer support surface 72 may include a bore formed therein for receiving a length of the second leg 88 of the biasing member. The legs 86, 88 can be fixed to the respective components by various joining mechanism including welding, soldering, adhesives, mechanical interference fit and the like. In FIG. 4A, when the biasing member 82 is a helical torsion spring, a moment can be created about the axis of the coil 84 such that each of the shells 60, 62 provides a radially inward retaining force Fs, opposing one another. The radially inward retaining force Fs can be applied along the recess along a plane that is preferably extends generally through the longitudinal axis LA of the prosthesis. The combined opposed radially inward retaining forces are greater than the radial expansion forces of the prosthesis such that the shells can retain the prosthesis in the compressed configuration.

FIGS. 4A-4C illustrate the operation of deployment device 10 in removing the shells 60, 62 of the retaining member 14 from prosthesis 15 for expansion thereof. FIG. 4A depicts the retaining member 14 in the closed position to retain the prosthesis 15 in the radially compressed configuration. The distal surface 28 of the distal portion 26 of the plunger 20 is at rest at the first position. At the first position, the distal surface 28 of the plunger 20 may be spaced from, or slightly contacting, the retaining engaging surface 77 formed by the inner engaging surfaces 74. The biasing member 82 can bias each of the shells 60, 62 in the closed position with the opposing radially inward retaining forces Fs.

An end user can place his or her palm and fingers around the intermediate body 34 in order to place the thumb on the plunger 20 for actuation of the plunger. Optionally, an end user can place his or her palm of a single hand on the proximal surface 40 of the proximal portion 22 of the plunger 20, and curl his or her one or more fingers of the same hand around the proximal portion 32 of the support frame 18 to place the fingers around the intermediate portion 30 of the support frame. The portions of the support frame 18 and the plunger 20 are configured to be manipulated and handled by the end user, and preferably sized to fit within a single hand of the end user to allow for operation by a single hand. With the retaining member 14 in the closed position and the plunger at the first position, the hand of the end user can apply a force F along the translational axis TA at the proximal surface 40 of the proximal portion 22 of the plunger 20, which is transmitted to the distal surface 28 of the distal portion of the plunger 20. Force F can be at least greater than the opposing radially inward retaining force Fs of each shell provided by the biasing member.

In FIG. 4B, under the force F, the proximal surface 40 of the plunger 20 is moved along the translational axis TA relative to the support frame 18 away from the first position in a closer proximity to the proximal portion 32 of the support frame 18. Consequently, the distal surface 28 of the distal portion 26 of the plunger 20 translates downward to an intermediate third position, between the first and second positions, slidably engaging the retaining engaging surface 77. The inner engaging surfaces 74 of shells 60, 62 and the confronting surfaces 71 begin to separate from one another as the shells 60, 62 begin to be pivotably displaced outward about the respective pivot axes. To this end, the surfaces defining the recesses 70 begin to move outward away from one another to permit the prosthesis to begin expanding to the expanded configuration. It is contemplated that the distal surface 28 of the plunger and the inner engaging surfaces 74 of the shells can be configured for smooth slidable engagement, such as being coated with a lubricious coating such as PTFE.

In FIG. 4C, under the force F, the proximal surface 40 of the plunger 20 is moved along the translational axis TA relative to the support frame 18 away from the first position in a closer proximity to the proximal portion 32 of the support frame 18. Consequently, the distal surface 28 of the distal portion 26 of the plunger 20 translates downward away from the third position to the second position, slidably engaging the inner engaging surfaces 74 of shells 60, 62. The inner engaging surfaces 74 of the shells 60, 62 and the confronting surfaces 71 are separated farther from one another as the shells 60, 62 are pivotably displaced outward about the respective pivot axes so that the retaining member 14 assumes the open configuration. To this end, the surfaces defining the recesses 70 are moved outward away from one another to permit the prosthesis to fully expand to the radially expanded configuration.

FIG. 5 depicts another embodiment of a deployment device 110 having the handle portion 112 and the retaining member 114 that can retain the prosthesis 15 in the radially compressed configuration. The handle portion 112 can include the actuation member 116, such as the plunger 120, slidably coupled to the support frame 118. In this embodiment, the device includes retractable ends that cover the outer ends of the prosthesis. For example, the retractable cuffs 200 are disposed at the axial ends 169A, 169B of the distal portion 168 of the shells 160, 162. The retractable cuffs 200 can be configured to facilitate insertion of the ends of the prosthesis 15 into the body vessel portions.

Figure 7:
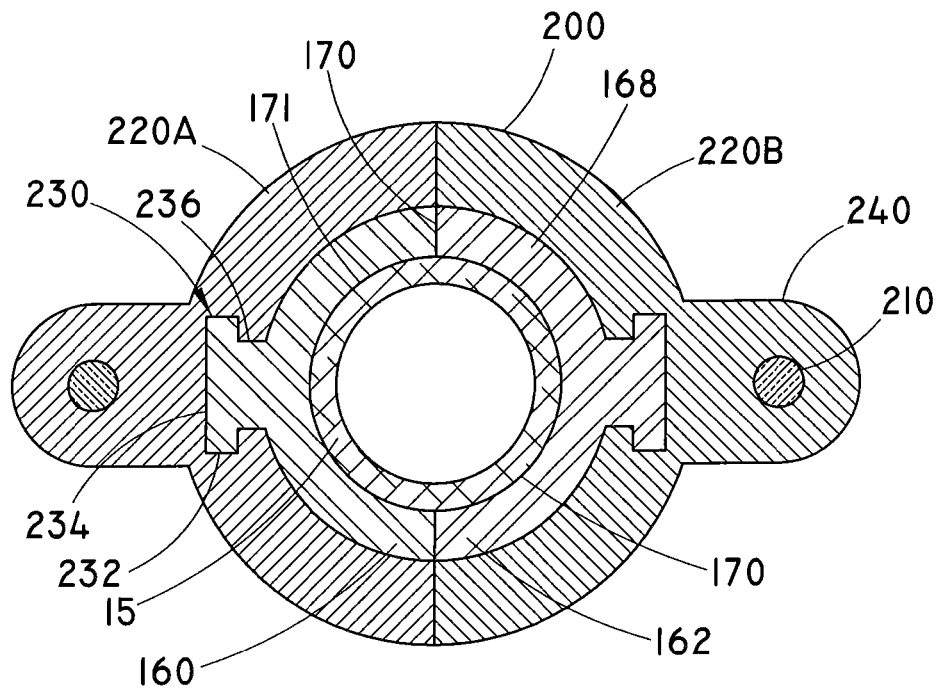
FIG. 7 is a transverse sectional view of the retractable cuff taken along lines 7-7 in FIG. 5.

For example, each of the shells 160, 162 include the proximal portion 166 hingedly attached to the support frame 118 and the distal portion 168. A biasing member (not shown) may bias the shells in the closed position. A support member 173 may extend between the proximal and distal portions 166, 168. The support member 173 can be located at an intermediate region of the proximal and distal portions, and preferably at the center of each such that the distal portion extends longitudinally beyond the support member. The longitudinal recess 170 can be formed in the confronting surface 171 of the distal portion 168 as shown in FIG. 7.

Figure 6:
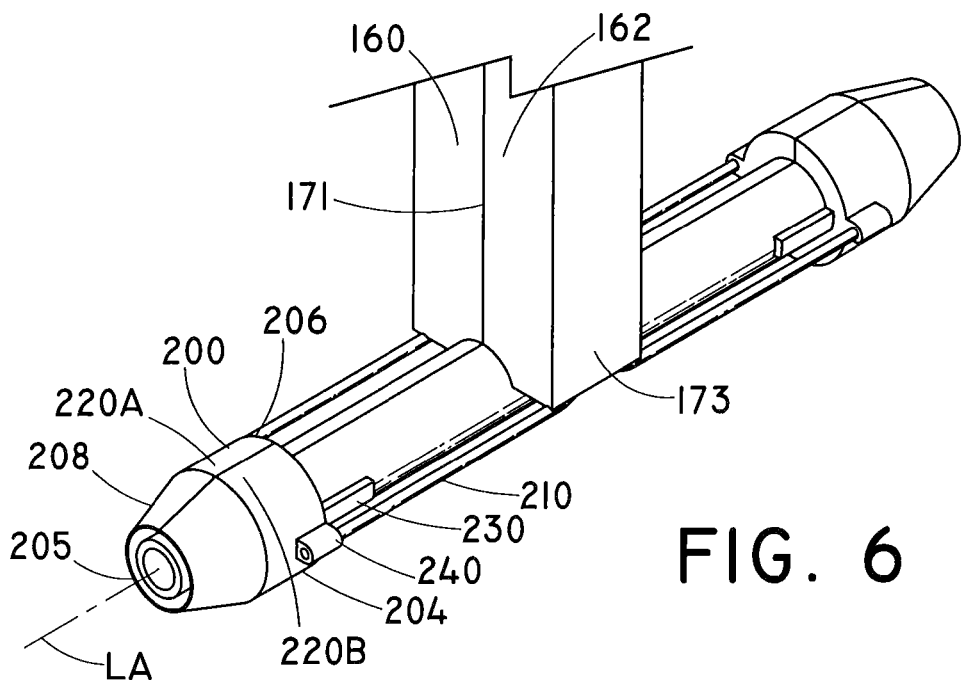
FIG. 6 is a perspective view of a retractable cuff coupled to the deployment device of FIG. 5.

In FIG. 6, the retractable cuff 200 is movable from the end of the prosthesis in a direction toward the middle of the prosthesis, with the ends of the prosthesis extending longitudinally beyond the ends of the distal portion 168. To this end, the retractable cuff is movable between a delivery configuration and a deployed configuration. The retractable cuff 200 can include a tubular body 204 having a first end opening 205 and a second end opening 206. The first end 205 of the body 204 may also be a tapered end 208 extending over the end of the prosthesis to facilitate insertion of the end of the prosthesis into the body vessel portion. In FIG. 5, in one example, a control member 210, such as a wire and/or rod, can be coupled to the retractable cuff 200, and an operable element, such as a pull tab 214, can be coupled to the control member 210. The pull tab 214 can be selectively operable to cause the retractable cuff 200 to move between the delivery and deployed configurations.

The body 204 of the retractable cuff 200 can extend longitudinally beyond the end of the distal portion 168 to surround the outer end of the prosthesis. The body 204 can be configured to slidably engage the outer surface of the distal portion 168. In one example, the retractable cuff 200 is splittable into two portions 220A, 220B so that when the shells 160, 162 are pivoted outward about the respective pivot axes the retractable cuff portions remain coupled to the respective shell. To facilitate coupling and slidability of the retractable cuff portions to the distal portions of the shells 160, 162, a track 230 can be included on the outer surface of the distal portion 168. A channel 232 can also be included along the inner surface of the retractable cuff portions 220A, 220B for slidably receiving the track 230. The track and the channel can be sized and shaped to prevent the channel from being pulled away from the track in an outward direction. To this end, the track and the channel can have an increasingly smaller cross-section in order to facilitate the mating relationship with one another. In the cross-sectional view of FIG. 7, the track 230 and the channel 232 can be t-shaped so that the head 234 of the track defines a repeatable and consistent sliding longitudinal pathway and the stem 236 permits the retention of the retractable cuff portions 220A, 220B from being easily removed in the outward direction.

Figure 8A:
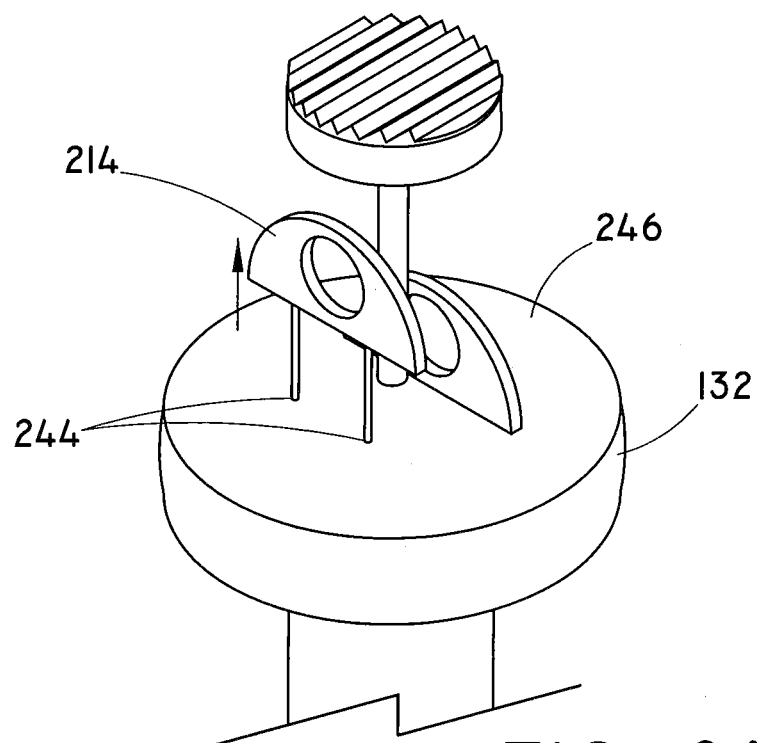
FIGS. 8A-8B are perspective views depicting operation of the retractable cuff of the deployment device of FIG. 5.

A first end of the control member 210 can be coupled to the retractable cuff portions 220A, 220B of each retractable cuff 200, for example, at a mounting portion 240 that is coupled to the outer surface of the body 204. The control member 210 can extend longitudinally along the longitudinal axis LA external to the distal portion 168 into an entry port 242 formed in the shells 160, 162. The control member 210 can be then redirected axially along the translational axis TA through a first conduit (not shown) formed in the shells 160, 162 and can exit through an exit port (not shown) formed in the inner engaging surface 174. The entry port 242 can be a rounded or tapered surface or can include a wheel to facilitate redirection and transmission of force of the control member. The control member 210 can continue along the translational axis TA through an entry port (not shown) of the support frame 118 and through a second conduit (not shown) formed in the support frame 118. The first and second conduits may be lubricated to facilitate movement of the control member. A second end of the control member 210 can extend beyond an exit port 244 formed in the proximal portion 132 of the support frame 118 so that the pull tab 214 is positioned along the surface 246 of the proximal portion 132, as shown in FIG. 8A. The pull tab 214 can be a ring structure having an aperture 248 formed therein sized for a finger of the end user to fit within. The pull tab 214 can have a planar surface 250 for contacting the planar surface 246 of the proximal portion 132.

Figure 8B:
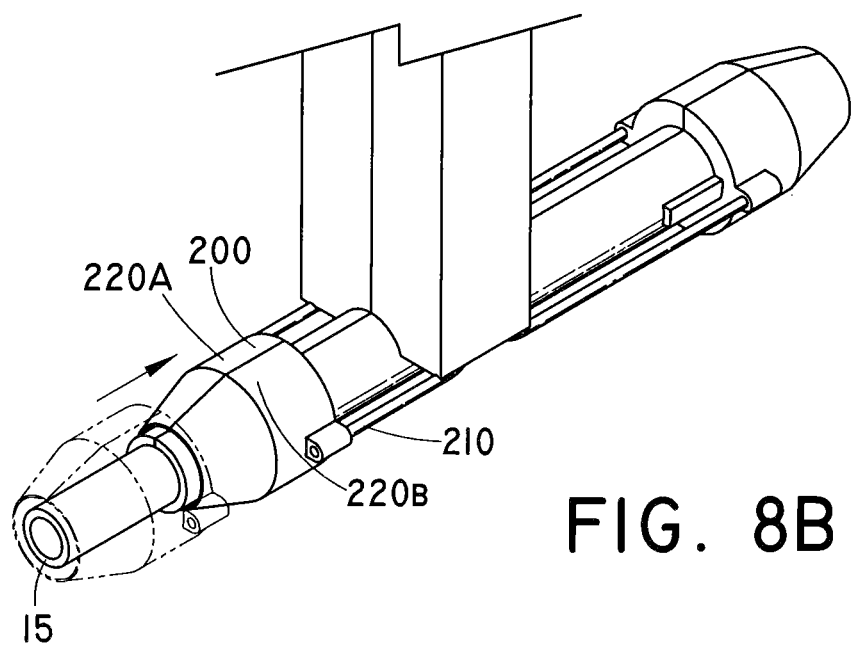

In FIGS. 8A-8B, the pull tab 214 can be selectively operable to cause the retractable cuff 200 via the control member 210 to move between the delivery configuration (shown in phantom lines) and the deployed configuration to allow for expansion of the respective end of the prosthesis. Thus, the pull tab 214 is movable between a first position where the retractable cuff 200 is in the delivery configuration, as shown in FIG. 5, and a second position where the retractable cuff 200 is in the deployed configuration, as shown in FIGS. 8A-8B. The pull tab 214 (two pull tabs shown) can be coupled to the retractable portion 220A via a first control member and to the retractable portion 220B via a second control member (shown as control member 210). Hence, a single pull tab 214 can be moved to the second position to remove simultaneously the retractable cuff portions 220A, 220B of a single retractable cuff 200 from one end of the prosthesis. The other pull tab can also be similarly moved to retract the other cuff. This arrangement can permit sequential deployment of the ends of the prosthesis into the body vessel portions. It is contemplated that a pull tab can be coupled to a single retractable cuff portion 220A or 220B such there are a total of four pull tabs, and two pull tabs can be pulled to remove the retractable cuff 200 from the end of the prosthesis. It is further contemplated that a single pull tab can be coupled to each retractable cuff such that a single pull tab 214 can be pulled to remove the retractable cuffs 200 from both ends of the prosthesis simultaneously. In one example, a biasing member such as a spring can be provided to bias the retractable cuffs in either the delivery or deployed configurations. Further, the retractable cuff portions 220A, 220B may be configured to lock in the deployed configuration after being moved there.

Operation of the deployment device will now be discussed. Although the discussion will focus primarily on the operation of deployment device 10, it can be appreciated by those skilled in the art that the other embodiments of the deployments devices described herein can be similarly operated and used.

FIGS. 9A-9F illustrate a method of treating a body vessel 320, found for example in the leg of a patient, which has previously been subjected to a traumatic episode, resulting in a portion 322 of body vessel 320 being torn away or otherwise severely damaged. Pre-surgery preparation has been applied to the leg and a trauma pathway may be formed therein in order to gain access to the body vessel and the damaged portion thereof. After clamping body vessel 320 on both ends of the portion 322 to restrict blood flow temporarily, the body vessel 320 can be cut or transected by the clinician into two portions 320A, 320B. The transection may be at the damaged portion 322 of the blood vessel 320 or as far away as necessary from the damaged portion to remove unhealthy portions of the body vessel or unrepairable portions of the body vessel. Sutures 324 can be attached to the end openings 325 of body vessel portions 320A, 320B to keep them fixed in place and opened to facilitate insertion of the prosthesis. Forceps may also be used in a similar manner. Any number of sutures can be used to retain the end openings 325 in the open position, although triangulation sutures can be sufficient, with each suture being about 120 degrees apart from the adjacent suture. A prosthesis is selected to have a radial expanded cross-section and a longitudinal length sufficient to bridge the body vessel portions 320A, 320B and radially fit within the body vessel portions.

Figure 9A:
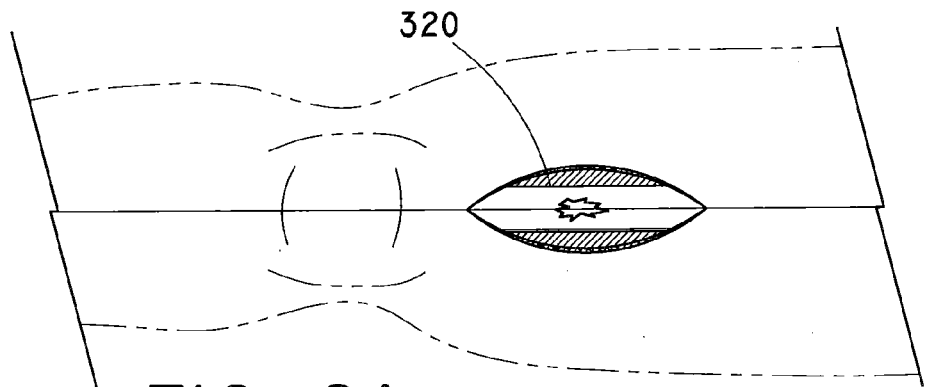
FIGS. 9A-9E illustrate a method of connecting body vessel portions with the deployment device of FIG. 1 to treat a body vessel.
Figure 9B:
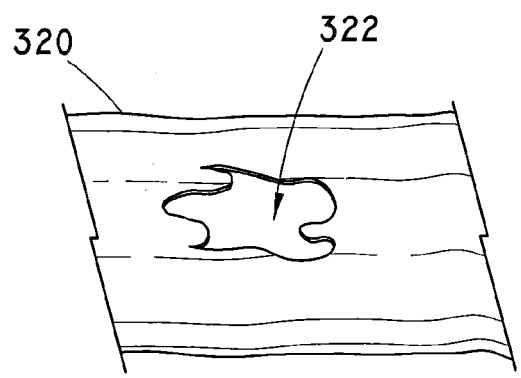
Figure 9E:
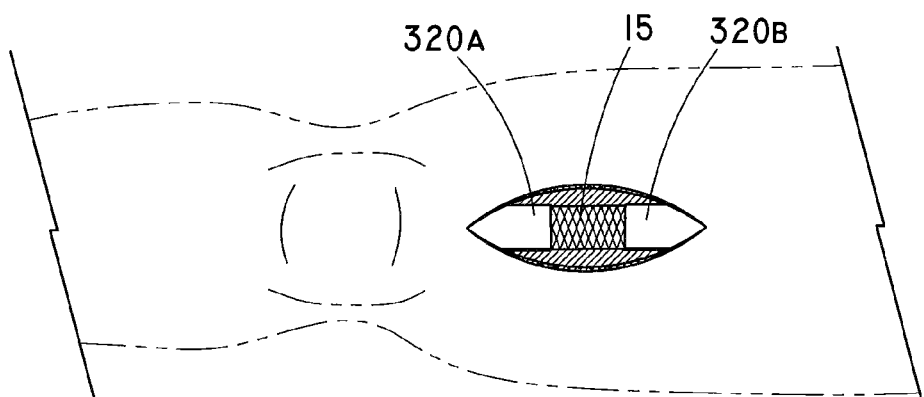
Figure 9C:
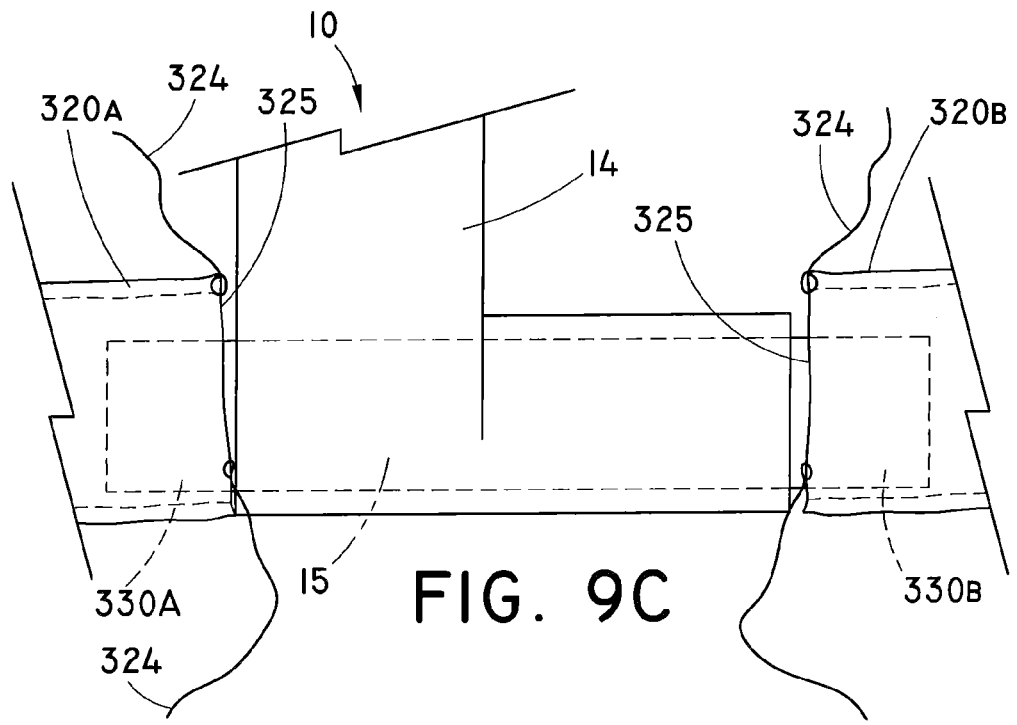

According to FIG. 9C, the prosthesis 15, which is preloaded within the deployment device 10, is shown being situated and oriented adjacent the body vessel portion 320A through the trauma pathway. The prosthesis 15, which is in the delivery, compressed configuration, is retained in the radially compressed configuration by the retaining member 14. The first outer end 330A of the prosthesis 15 can be inserted into vessel portion 320A by a sufficient distance for the purposes of engagement and/or anchoring. It is preferred that the vessel portion initially selected be the non-blood supplying vessel end. The vessel portion 320A may be manually pulled over the first outer end 330A of the prosthesis 15. The deployment device 10 and the prosthesis 15 can then be manipulated in order to introduce a second outer end 330B of the prosthesis 15 into the vessel portion 320B by a sufficient distance for the purposes of engagement and/or anchoring.

Figure 9D:
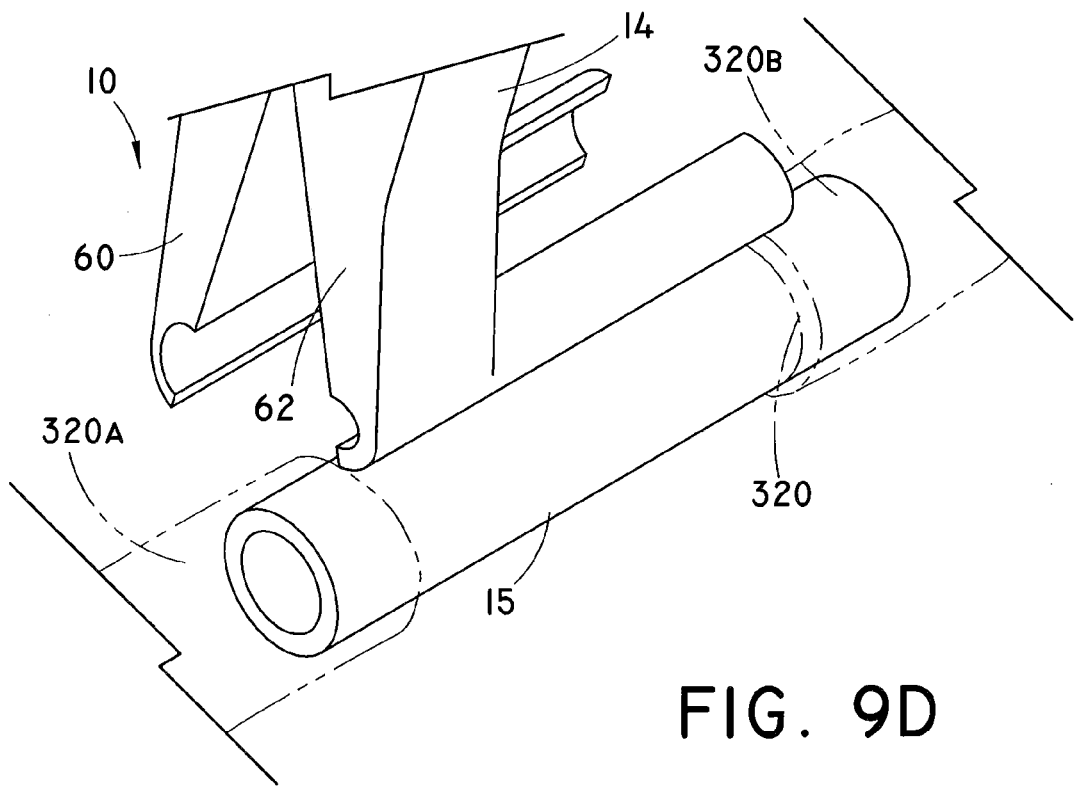

In FIG. 9D, after insertion of both outer ends 330A, 330B of the prosthesis 15 into the end opening 325 of the respective portions 320A, 320B of the body vessel 320, the actuation member can be operated to pivot the desired shells 60, 62 of the retaining member 14 away from prosthesis 15. This can permit expansion and engagement of a portion of prosthesis 15 along the wall of the vessel portions 320A, 320B. The vessel portions 320A, 320B can now be sealably engaged to first and second outer ends 330A, 330B of the prosthesis 15. Accordingly, the prosthesis 15 is fully deployed to bridge the first and second portions 320A, 320B of the transected body vessel 320 to form a conduit for blood flow. The sutures 324 can then be removed. Preferably, portions of the exterior surfaces of the prosthesis sealably engage with the luminal walls of the body vessel to inhibit leakage of blood and to force blood to flow throughout the body vessel during emergency surgery, and particularly to obtain hemostasis while maintaining blood perfusion. FIG. 9E shows the prosthesis 15 deployed and interconnecting the body vessel portions 320A, 320B within the leg of the patient. The prosthesis 15 can be adapted for permanent placement within the patient, thereby obviating a need for subsequent surgical intervention.

Figure 10C:
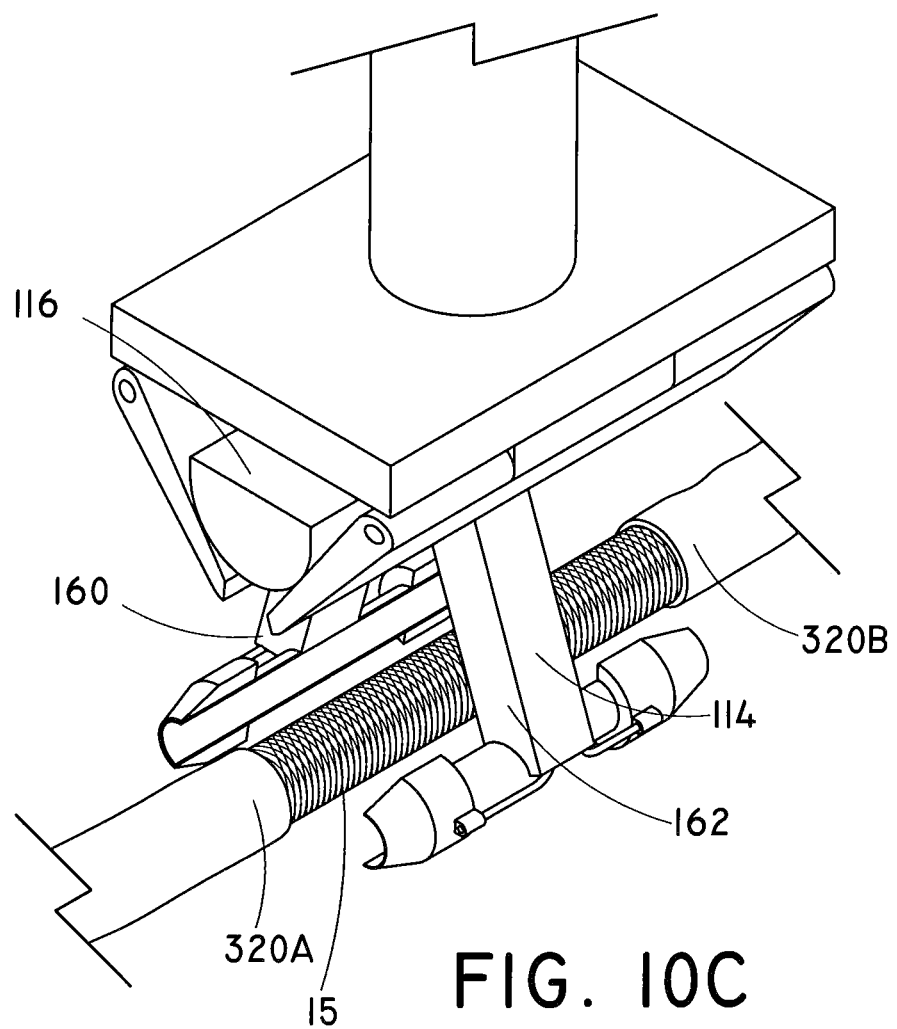

FIGS. 10A-10C illustrate operation of the device 110 that includes the retractable cuffs 200. According to FIG. 10A, the prosthesis 15, which is preloaded within deployment device 110, is shown being situated and oriented adjacent the body vessel portions 320A, 320B through the trauma pathway. The prosthesis 15, which is in the delivery, compressed configuration, is retained in the radially compressed configuration by the retaining member 114. The first and second outer ends 330A, 330B of prosthesis 15 are retained in the compressed configuration by the retractable cuff 200 that is in the delivery configuration. The cuffs 200 which cover the outer ends of the prosthesis can be inserted into the respective vessel portions 320A, 320B by a sufficient distance for the purposes of engagement and/or anchoring.

In FIG. 10B, the pull tabs 214 can be withdrawn to the second position, in the direction of arrows 340, sequentially or simultaneously as described herein, to cause the retractable cuff 200 to move to the deployed configuration to allow for expansion of the respective first and second outer ends 330A, 330B of prosthesis 15. Here, the outer ends of the prosthesis may be in engagement along the wall of the vessel portions 320A, 320B. Optionally, the outer ends of the prosthesis may expand less than the cross-sectional area of the body vessel. This removes the cuffs from the body vessel so that when the retaining member is moved to the open position the cuffs have sufficient clearance with respect to the body vessel portions. With the retraction cuffs in the deployed configuration, the actuation member 116 can be moved relative to the support frame in the direction of the arrow 350. As a result, the shells 160, 162 of the retaining member 114 can move away from the prosthesis 15, as shown in FIG. 10C. This can permit full expansion and engagement of a portion of the prosthesis 15 along the wall of the vessel portions 320A, 320B.

FIGS. 11-14 depict another embodiment of a deployment device 410 having the handle portion 412 and the retaining member 414 that can retain the prosthesis 15 in the radially compressed configuration. The handle portion 412 can include the actuation member 416 slidably coupled to the support frame 418. In this embodiment, the retractable cuffs 419 are disposed at the axial ends 469A, 469B of the distal portion 468 of the shells 460, 462.

The actuation member 416 can include a first or proximal portion 422, an intermediate shaft 424, and a second or distal portion 426 coupled to one another. The support frame 418 can include a tubular body 430 that can have a proximal portion coupled to the handle portion 412, an intermediate portion 434, and a distal portion 436 coupled to one another. The tubular body 430 can define a passageway (not shown) about the translational axis TA that can extend through the tubular body. The passageway is sized to receive the intermediate shaft 424 so that the actuation member is capable of being translated along the translational axis between a first position and a second position. The device 410 may include a biasing member such as a spring that is configured to bias the retaining member in the closed position when the actuation member is in the first position. The biasing member can also be coupled to the actuation member, such as within the body 430, to bias the actuation member in the first position, as can be appreciated by those skilled in the art. The proximal portion 422 can have an operable element, such as, e.g., a longitudinal dial 435 that is movable, such as e.g., downward, within a slot formed in the support frame 418 to cause the shells to pivot to the open position. The dial 435 may extend outwardly from a front face of the handle portion.

FIG. 12 depicts the distal portion 426 that can extend distally beyond a recessed notch 437 formed in the distal portion 436 of the support frame. The distal portion 426 can be a downward C-shaped body having a pair of legs 440 extending downwardly for coupling to the shells 460, 462. The distal portion 436 with the notch 437 formed therein from the end of the support frame in a proximal direction can define a pair of finger members 439. The notch 437 is sized to receive the proximal portion 466 of the shells. Further, the proximal portion 466 of the shells can be placed adjacent to one another and together sized to fit between the legs 440 of the distal portion 426.

The shells 460, 462 together are configured to define the prosthesis retaining chamber 464 about the longitudinal axis LA of the prosthesis when the retaining member is in the closed position. Each of the shells can include the proximal portion 466 and the distal portion 468. The longitudinal recess 470 can be formed in the confronting surface 471 of the shell along the distal portion, such as shown in FIG. 13. The proximal portion 466 of the shells can be coupled to the distal portion 436 of the support frame 418 and the distal portion 426 of the actuation member 416. In one example, a pivot rod 441 may be extended laterally across the notch 437 to be fixed in a secured position with the finger members 439. The proximal portion 466 of the shells can have a bore extending laterally through the body of the shells for receiving the pivot rod 441. To this end, the shells 460, 462 can pivot about the pivot rod 441 between the closed position (FIG. 13) and the open position (FIG. 14) for delivery and deployment of the prosthesis.

Further, the proximal portion 466 of the shells can have an elongate slot 443 extending laterally through the body of the shells, as shown in FIG. 14. The first end 444A of the slot 443 can be formed in a central part of the shell and the second end 444B of the slot 443 may terminate closer to the edge of the shell than the first end. A control pin 445 can be extended laterally in order to be fixed in a secured position with the legs members 440 and to be received by the slots 443. When the actuation member 416 is in the first position, the control pin 445 is positioned at the first end of the slots 443 that overlap one another when the shells are in the closed position shown in FIG. 13. With movement of the actuation member 416 toward the second position, such as downward movement, the control pin 445 slidably engages the edges 447 that define the slot 443 toward the second end 444B of the slots, thereby causing the shells to pivot farther away from each other toward the open position as shown in FIG. 14. The control pin 445 can be translated along the translational axis and be moved relative to the pivot rod 441 that is in a fixed position. When the actuation member 416 is in the second position, the control pin 445 is positioned at the second end 444B of the slots 443 to cause the first end 444A of the slots to pivot away from each other and the shells to move to the open position, as shown in FIG. 14.

Referring back to FIG. 11, the retractable cuffs 419 can extend laterally beyond the sides 469A-B of the distal portion 468 to surround the outer ends of the prosthesis. To facilitate coupling and slidability of the retractable cuffs relative to the distal portions of the shells 460, 462, one or more tracks 463, e.g., three tracks are shown at about 60 degrees apart, can be included on the outer surface of the distal portion 468, as shown in FIG. 13. One or more channels 465 can also be formed along the inner surface of the retractable cuffs for slidably receiving the corresponding track 463. The track 463 and the channel 465 can be sized and shaped to prevent the channel from being pulled away from the track in an outward direction. To this end, the track and the channel can have an increasingly smaller cross-section to mate with another. In one example, the track can be circular with an increasingly smaller cross-section toward the surface of the cuff, and the channel can be circular shaped with an increasingly smaller cross-section toward the surface of the shell, as shown in FIGS. 13-14. The retractable cuff 419 can include a radial flange sized greater than the vessel. The radial flange can function as a physical stop to control the insertion distance of the cuff within the vessel portions. The cuff may also have a tapered outer surface to facilitate insertion into the vessel portion.

Figure 11:
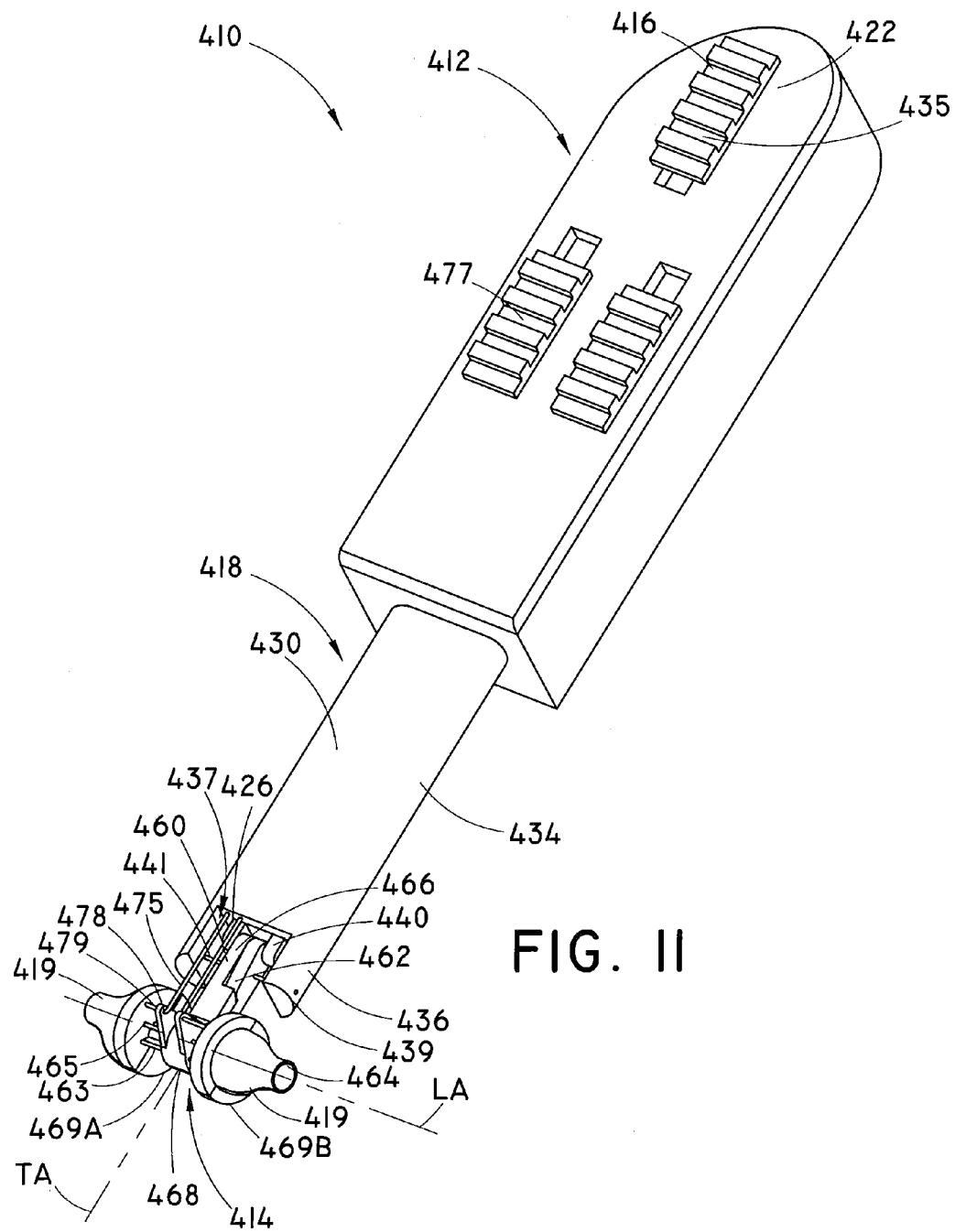
FIG. 11 is a perspective view of another example of a deployment device.

In FIG. 12, the control member 475 can be coupled between the retractable cuff 419 and one or more operable elements, such as a longitudinal dial 477, which is shown as two dials in FIG. 11. The dial 477 can be movable within a slot formed in the handle portion 412. The dial 477 may extend outwardly from a front face of the handle portion, and can be located underneath the dial 435. The dial 477 can be selectively operable to move the retractable cuff 419 between the delivery and deployed configurations. A first end of the control member 475 can be coupled to the retractable cuffs 419. The control member 475 can extend from the first end longitudinally along the longitudinal axis LA into a port 478 that formed in an ear portion 479 that extends outward from the shells 460, 462. The port 478 may be tapered to facilitate movement of the control member between the longitudinal and translational axes. The control member 475 can extend through a conduit formed in the support frame 418 so that a second end of the control member 475 is coupled to the dial 477. In one example, the control member 475 can include a flexible wire, such as stainless steel or other known metal suitable for medical procedures. In another example, the control member is a hybrid member, being formed of a wire from the first end of the control member to at least the ear portion, and being formed of a rigid shaft, such as a stainless steel shaft or other biocompatible metal or plastic shaft, to facilitate transmission of forces from the dial.

The dial 477 can be selectively operable, such as upward, to cause the retractable cuff 419 via the control member 475 to move between the delivery and deployed configurations to allow for expansion of the respective end of the prosthesis such as shown in FIGS. 10B-10C. The dial 477 is movable within the slot between a first position where the retractable cuff 419 is in the delivery configuration, and a second position where the retractable cuff 419 is in the deployed configuration. Each of the dials 477 can be coupled to one of the retractable cuffs 419 for sequential operation, although one dial may be coupled to both of the two retractable cuffs for simultaneous operation. Operation of the device 410 with movement of the shells and the cuffs to deploy a prosthesis to treat a body vessel can be gained with additional reference to FIGS. 9A-9E and FIGS. 10A-10C, as can be appreciated by one skilled in the art.

Figure 15A:
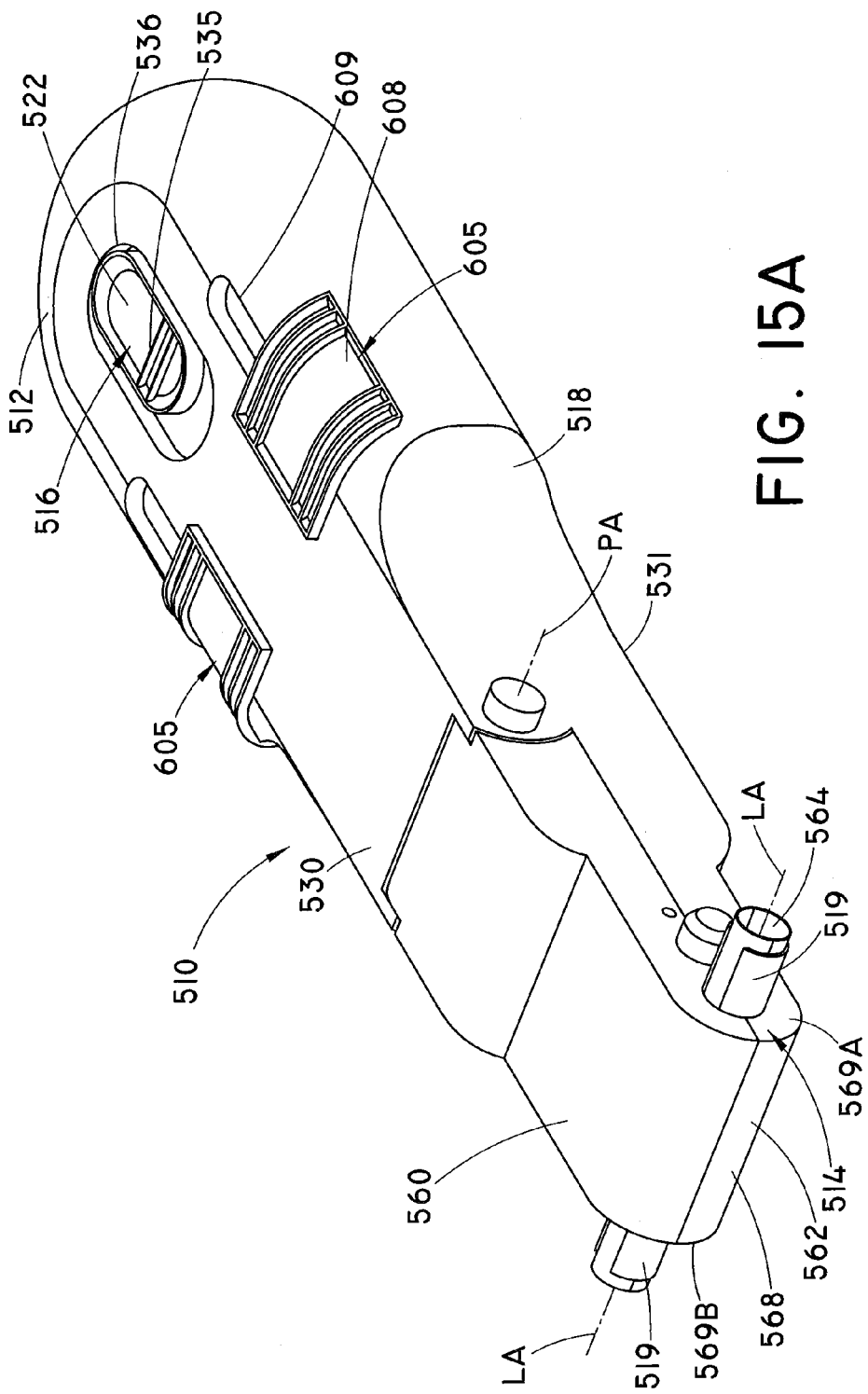
FIG. 15A is a perspective view of another example of a deployment device, with a retaining member in the closed position.

FIGS. 15A-15B depict another embodiment of a deployment device 510 having the handle portion 512 and the retaining member 514 that can retain the prosthesis in the radially compressed configuration. The handle portion 512 can include the actuation member 516 slidably coupled to the support frame 518. In this embodiment, the actuation member 516 and other movable components can be fully enclosed within the housing of the support frame 518 and the retaining member 514. This arrangement can protect the body and various body tissues from inadvertent harmful contact from the movable components of the device, as well as providing the movable components freedom to move without being obstructed from portions of the body. FIGS. 15A-15B illustrate the movement of some of the components. For example, FIG. 15A shows the actuation member 516 in the first position, the retaining member 514 in the closed position, and the retractable cuffs 519 in the delivery configuration. FIG. 15B shows the actuation member 516 in the second position, the retaining member 514 in the open position, and the retractable cuffs 519 in the deployed configuration.

Figure 16:
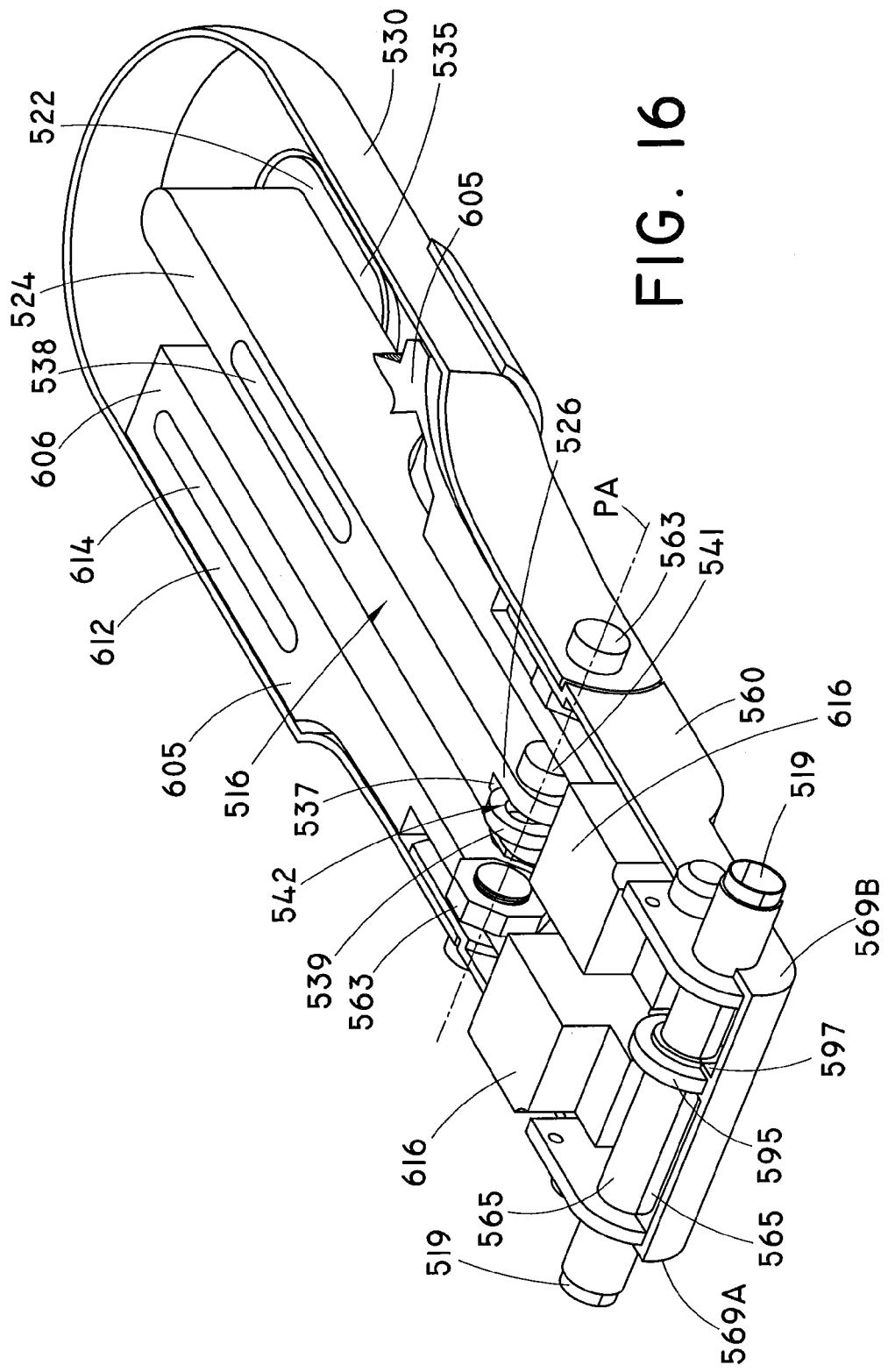
FIG. 16 is a perspective view of the deployment device of FIG. 15A, with the bottom half of the device removed.

FIG. 16 illustrates the device 510 with one-half (i.e., the bottom half) of the housing of the support frame 518 and the second shell 562 removed in order to gain an appreciation of the movable components within the housing. The actuation member 516 can include a first or proximal portion 522, an intermediate shaft 524, and a second or distal portion 526 coupled to one another. The support frame 518 can be a hollow housing having a first portion 530 and a second portion 531 (shown removed in FIG. 16) that together define a cavity. The proximal portion 522 of the actuation member can have an operable element coupled thereto, such as, e.g., a longitudinal dial 535, that is movable, such as e.g., downward, within a slot 536 formed in the first portion 530 in order to move the retaining member 516 to the open position. The dial 535 may extend outwardly from a front face of the handle portion. The intermediate shaft 524 can have a longitudinal slot 538 formed therein. The slot 538 can fit over a longitudinal protrusion (not shown) formed on the inner surface of the second portion 531 of the support frame 518 to form a guide or track system for facilitating movement and stability of the actuation member relative to the support frame. The device 510 may include a biasing member (not shown) such as a spring to bias the actuation member in the first or second position and thus the retaining member in the closed position or open position, as can be appreciated by those skilled in the art.

FIG. 15B depicts the second shell 562 integral with the second portion 531 of the support frame, whereas the first shell 560 is hingedly attached to the first portion 530 of the support frame. FIG. 16 shows a pair of opposite sidewalls of the first shell 560 hingedly attached to a pair of opposite sidewalls of the first portion 530 at the pivot attachment 563. The pivot attachment 563 between the first shell 560 and the first portion 530 can be formed with various hinge mechanisms known in the art such as a rivet, nut/bolt, or other mechanical fasteners, which are inserted through openings formed in the respective components. The first shell 560 is also hingedly attached to the distal portion 526 of the actuation member. For example, the distal portion 526 can have a recessed notch 537 formed in the end of the shaft 524 in a proximal direction to define a pair of finger members. The notch 537 is sized to receive an ear member 539 that extends outwardly from the inner surface of the first shell 560. A coupling pin 541 can be extended through openings formed in the finger members and in the ear member 539 to form the hinge attachment 542. The opening in the ear portion 539 can be an elongate opening, such as shown in FIG. 16. The coupling pin 541 can rest at one end of the elongate opening when the actuation member 516 is at the first position. The coupling pin 541 can be moved within the opening toward the opposite end of the elongate opening when the actuation member is moved toward the second position. The plane, along which the coupling pin 541 is moved along, can remain offset from the pivot axis PA defined by the pivot attachments 563 to create a moment and rotation of the first shell 560 about the axis PA. To this end, linear movement of the actuation member 516 toward the second position urges the first shell 560 to pivot about the pivot axis PA of the pivot attachment 563 away from the second shell 562. This movement moves the retaining member 514 to the open position, such as shown in FIG. 15B, so that the intermediate segment of the prosthesis is permitted to move the expanded configuration.

The shells 560, 562 together are configured to define the prosthesis retaining chamber 564 about the longitudinal axis LA of the prosthesis when the retaining member 514 is in the closed position, as shown in FIG. 15A. A longitudinal recess may be formed in the confronting surfaces of the shells to form the retaining chamber. In another example, an insert 565 can be located within each of the shells 560, 562 to reinforce the retention of an intermediate segment of a prosthesis. A pair of inserts 565 together define a tubular chamber, as shown in FIG. 16, that is sized to receive at least a portion of the prosthesis. The inserts 565 can be made of a rigid material such as metal or polymer. Each insert 565 can be attached to a corresponding shell, and the inserts 565 are splittable upon movement of the shells 560, 562 to the open position.

Figures 17A, 17B:
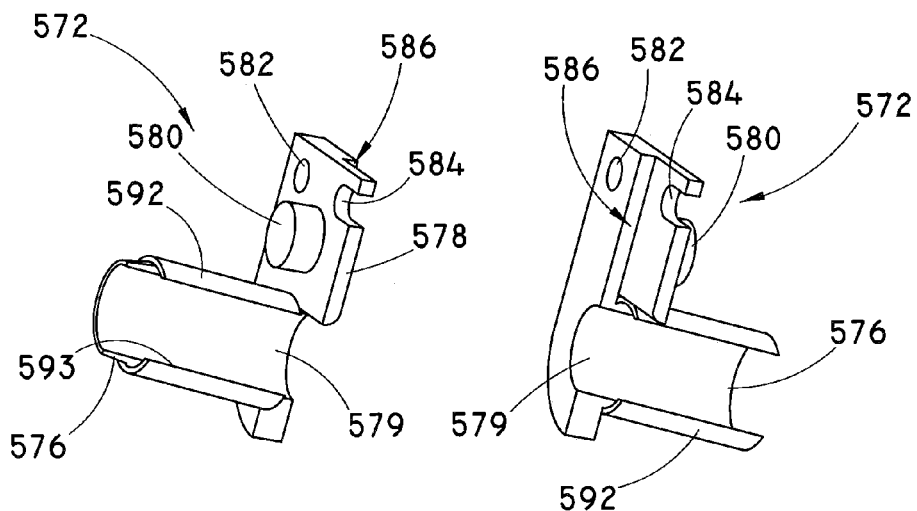
FIGS. 17A-17D are perspective view of various aspects of one example of retractable cuffs provided with the deployment device of FIG. 15A.
Figures 17C, 17D:
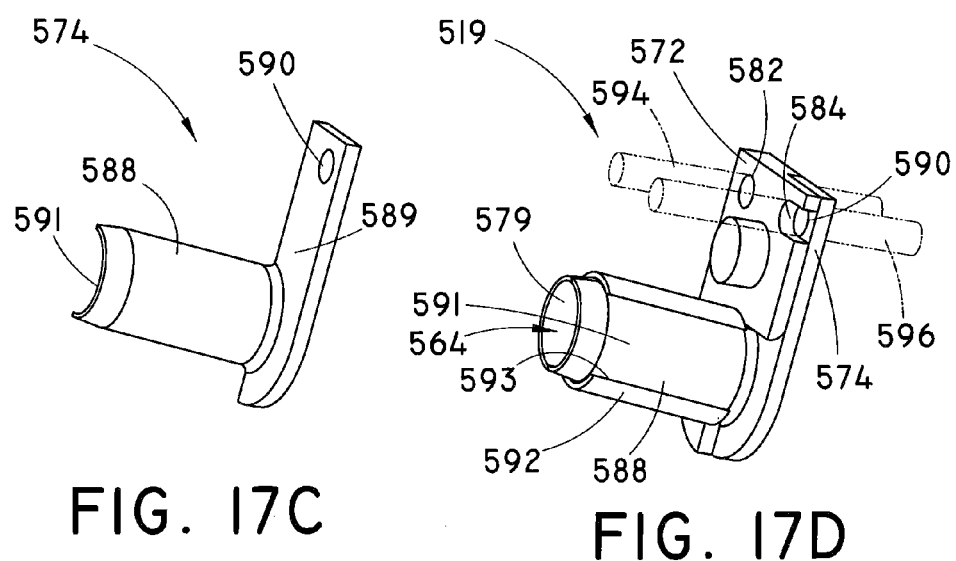

FIGS. 15A and 16 illustrate the retractable cuffs 519 extended outward from the lateral sides 569A, 569B of the distal portion 568 of the shells 560, 562 through an opening formed by the shells. FIGS. 17A-17D show various aspects of the retractable cuffs. Here, the retractable cuff has a first cuff portion 572 (FIGS. 17A-17B) and a second cuff portion 574 (FIG. 17C) that couple to one another as shown in FIG. 17D. In FIGS. 17A-17B, the first cuff portion 572 can include a chamber portion 576 and a plate 578 attached to one end of the chamber portion 576 and extending generally perpendicular thereto. The first cuff portion 572 is typically associated with the second shell 562. An opening in the plate 578 and the opening defined by the chamber portion 576 together define a first recess 579. The plate 578 can include a nub 580 on one lateral side of the plate, which extends along the same direction as the chamber portion. A through bore 582 and an open recess 584 can be formed in the plate 578, e.g., along the proximal portion of the plate, generally along the same direction as the chamber portion. A notch 586 can be formed in the plate, generally perpendicular to the chamber portion, and is sized to receive the second cuff portion 574.

In FIG. 17C, the second cuff portion 574 can include a chamber portion 588 and a plate 589 attached to one end of the chamber portion 588 and extending generally perpendicular thereto. The second cuff portion 574 is typically associated with the first shell 560. A through bore 590 can be formed in the plate 589, e.g., along the proximal portion of the plate, generally along the same direction as the chamber portion. An opening in the plate 589 and the opening defined by the chamber portion 588 together define a second recess 591.

FIG. 17D shows the first cuff portion 572 coupled to the second cuff portion 574 such that the first and second recesses 579, 591 form a tubular segment of the prosthesis retaining chamber 564. The open recess 584 of the first cuff portion 572 is in communication with the through bore 590 of the second cuff portion 574. The tubular segment defined by the first and second recesses 579, 591 can be sized larger than the size of the tubular chamber defined by the inserts 565, if employed. Such tubular segment of the first and second portions 572, 574 can fit over and slide along the tubular chamber defined by the combined inserts 565. To reinforce the radial strength of the cuff, a retention member 592 can fit over the respective chamber portions 576, 588 of the cuff. The retention member 592 can have a C-shape and is sized circumferentially at least to cover the seams formed by the coupled chamber portions of the cuffs. The retention member 592 can be attached or otherwise remain associated with the first cuff portion 572, such as being formed integrally with the first portion. The first and second cuff portions 572, 574 are capable of being split apart upon relative movement between the first and second shells 560, 562. To this end, the retention member 592, which is fitted over the chamber portion 576 of the first cuff portion 572, can have a slot 593 that is sized to permit the passage of the chamber portion 588 of the second cuff portion 574 therethrough.

In FIG. 17D, a pair of rods 594, 596 (shown in dashed lines) can be extended laterally between the sidewalls of the respective first and second shells and coupled thereto to provide guides for the retractable cuffs 519. For example, a first rod 594 can be coupled to the first shell 560, as shown in FIG. 19A. The second cuff portion 574 may be retained within the first shell by the first rod 594. The first rod 594 can be received within the through bore 590 of the second cuff portion 574 and the open recess 584 of the first cuff portion 572 of each of the cuffs. A second rod 596 can be coupled to the second shell 560. The first cuff portion 572 may be retained within the second shell by the second rod. The second rod 596 can be received within the through bore 582 of the first cuff portions 572 of each of the cuffs. The cuffs 519 can be moved longitudinally inward along the rods 594, 596, which are typically in a parallel orientation with one another, between the delivery and deployed configurations. The open recess 584 of the first cuff portions that are associated with the second shell 562 can allow the first rod 594 that is associated with the first shell 560 to pass therethrough during movement of the shells to the open position. A radial protrusion 595 can be formed on the inserts 565 to facilitate attachment to the support member. For example, an internal rib 597 with a recess formed therein can be provided along the inner surfaces of the shells to receive the inserts and the radial protrusion. The rib can also provide a physical stop for the cuffs when moving inward.

In FIGS. 18-19, a release member can be associated with each of the cuffs to provide selective movement of the cuffs. The release members 605 can be disposed within the support frame 518. A proximal portion 606 of the release member can have an operable element coupled thereto, such as, e.g., a longitudinal dial 608 shown in FIG. 15A, that is movable, such as e.g., upward, within a slot 609 formed in the first portion 530 in order to move the release members from the first position to the second position. The dial 608 may extend outwardly from a front face of the handle portion. The dial 608 can be selectively operable to move the retractable cuff 519 between the delivery and deployed configurations. The dial 608 is movable within the slot 609 between a first position where the retractable cuff 519 is in the delivery configuration, and a second position where the retractable cuff 519 is in the deployed configuration. Each of the dials 608 can be operable for independent sequential retraction of the cuffs or for simultaneous retraction of the cuffs. An intermediate shaft 612 of the release member can have a longitudinal slot 614 formed therein. The slot 614 can fit over a longitudinal protrusion (not shown) formed on the inner surface of the second portion 531 of the support frame 518 to form a guide or track system for facilitating movement and stability of the release members relative to the support frame.

When in the first position, the distal end 616 of the release member 605 is sized to fit within a space between the internal rib 597 and the plate of the cuffs 519 to maintain the cuffs in the delivery position over the outer end of the prosthesis 15, as shown in FIG. 18A. In this position, the cuff 519 makes up a portion of the prosthesis retaining chamber 564. Upon removal of the distal end 616 from such space, the cuff 519 is capable of moving inward to the deployed configuration, as shown in FIG. 19A. A biasing member 620 such as a spring can be coupled between the retractable cuff 519 and the support frame 518. The biasing member 620 can be configured to bias the cuff in either the delivery or deployed configurations. For example, the biasing member 620 can bias the cuff in the deployed configuration such that upon removal of the release member 605 the cuff 519 can automatically move from the delivery configuration to the deployed configuration, such as shown in FIGS. 19-19A. The biasing member 620 can be oriented along the longitudinal axis LA to maximize the spring force of the biasing member to overcome the frictional and engagement forces between the cuff and the prosthesis. This arrangement permits the outer end of the prosthesis to be expanded, while the intermediate segment of the prosthesis is retained by the retaining member. One end of the biasing member 620 can fit over the nub 580 of the cuff 519 and the opposite end can be received in the cavity of an end cap 622 formed in the sidewall of the support member. The end cap 622 can be sized to receive the nub 580 when the biasing member 620 is fully axially compressed when the release member is at the first position, such as shown in FIG. 18A. Operation of the device 510 with movement of the shells and the cuffs to deploy a prosthesis to treat a body vessel can be gained with additional reference to FIGS. 9A-9E and FIGS. 10A-10C, as can be appreciated by one skilled in the art.

FIG. 20 illustrates another embodiment of a deployment device 700 having a retractable cuff that can be directly moved by the end user. The retractable cuff 710 has similar aspects to the retractable cuff 519 shown in FIGS. 17A-17C. The retractable cuff 710 includes a first cuff portion 712 associated with the first shell (not shown) and a second cuff portion 714 associated with the second shell 715. The first cuff portion 712 can include a chamber portion 720 and a plate 722 attached to one end of the chamber portion 720 and extending generally perpendicular thereto. An opening in the plate and the opening defined by the chamber portion together define a first recess. A through bore 725 (two shown) can be formed in the plate. The second cuff portion 714 can include a chamber portion 730 and a plate (not shown) attached to one end of the chamber portion 730 and extending generally perpendicular thereto. An opening in the plate and the opening defined by the chamber portion together define a second recess.

The first cuff portion 712 can be coupled to the second cuff portion 714 such that the first and second recesses together form a tubular segment 735 of the prosthesis retaining chamber. A pair of rods 736 can be extended laterally between the sidewalls of the first shell and coupled thereto to provide guides for the retractable cuffs. For example, the first cuff portion 712 can be retained within the first shell by the rods 736. The rods 736 are received within the through bores 725 of the first cuff portion 712. The cuffs 710 can move along the rods 736 between the delivery configuration shown in FIG. 20 and the deployed configuration where the cuffs 710 are removed from the outer segments of the prosthesis. When the shells are separated from one another to the open position, the first and second cuff portions 712, 714 can be separated from one another to allow for expansion of the intermediate segment of the prosthesis.

An operable element 740 can be coupled to each of the retractable cuffs 710. The operable element 740 can extend out from an aperture 742 formed in the support frame 745. The operable element 740 can have a notch 746 formed therein. The notch 746 is sized to receive a track 748 provided with the support frame that provides a guide surface for the operable element 740 when moving toward the middle of the support frame 745. A support arm 750 can couple the operable element 740 directly to the first and second cuff portions 712, 714. To operate the retractable cuff 710, a force is applied to the operable element 740 in the inward direction, represented by arrow 755 along the direction of the longitudinal axis LA when the shells are in the closed position. The operable element 740 can be guided along the track 748 and the first and second cuff portions 712, 714 can move with the operable element 740 along the rods 736 in a corresponding manner. Each operable element 740 can be moved independent from one another for simultaneous or sequential movement of the cuffs. Operation of the device with movement of the shells and the cuffs 710 to deploy a prosthesis to treat a body vessel can be gained with additional reference to the figures, such as FIGS. 9A-9E and FIGS. 10A-10C, as can be appreciated by one skilled in the art. It can be appreciated that the device 700 includes a retaining member, which can be moved by the various mechanisms described herein, in order to allow for expansion of the prosthesis.

FIGS. 21-25 illustrate another embodiment of a deployment device 800 having many of the features described in the previous embodiments. For example, the device 800 has the handle portion 812, the retaining member 814 that can retain the prosthesis in the radially compressed configuration, and the actuation member 816 with the dial 817 at the proximal end thereof. The actuation member 816 is movable between first and second positions to move the retaining member between the closed position (FIG. 21) and the open position (FIG. 22), respectively. FIG. 22 illustrates the entire retaining member 814 is axially movable along the translational axis TA when moving between the open and closed positions.

FIG. 23A-23B illustrate example construction of the actuation member 816 and the release members 819. The actuation member 816 includes a distal end 820 having a U-shape. A pin 824 can be included between the two legs of the distal end 820. The pin 824 is shown to carry several components and can provide a common pivot axis for such components. For example, the shells or clamps 830, 831 and the first and second cuff portions 832, 834 of the retractable cuffs 835 are capable of rotating about the pin 824. The biasing member 838, shown as a spring, is disposed to surround the pin 824, extending between the inner surface of the legs of the distal end 820 and the first cuff portion 832 in order to bias the cuffs in the retracted position or deployed configuration. To maintain the cuffs 835 in the delivery configuration, the distal end 840 of the release member 819 is positionable in between the second cuff portion 834 and the proximal portion 842 of the shells 830, 831. For example, the distal end 840 of the release member can be a C-shaped tubular member to fit around the pin 824. The first of the release members 819 is shown in the delivery position to maintain the first of the cuffs 835 in the delivery configuration. The second of the release members 819 is shown in the deployed position to allow the second of the cuffs 835 to move to the deployed configuration, which movement can be facilitated by the biasing member 838.

FIG. 24 illustrates the distal end of the shell, represented by the shell 831. When the shells 830, 831 are in the closed position, the shells 830, 831 together define an inner tubular member having a chamber extending therethrough for retaining the prosthesis and an outer tubular member positioned in a spaced relationship relative to the inner tubular member to define a curved tracking channel for receiving the cuffs 835. To this end, the shell 831 includes an inner semi-circular portion 845 that defines a portion of the inner tubular member and an outer semi-circular portion 847 that defines a portion of the outer tubular member. As shown, the cuff portion, represented by the first cuff portion 832, is shaped and sized to fit within the tracking channel 849, over the inner semi-circular portion 845 and within the outer semi-circular portion 847.

FIG. 25 illustrates another aspect of the distal end of the shell 831. The proximal portion 842 of the shell 831 is angled in a manner to place the opening 850 that receives the pin 824 at the apex 852 of the proximal portion 842. The proximal end 854 is engaged with a guiding surface 855 that protrudes from the inner wall 856 of the housing (i.e., the bottom half) of the support frame to define a cam configuration. The guiding surface 855 is shaped to change in elevation, e.g., the guiding surface 855 is curved outward away from the inner wall 856. The curve of the guiding surface 854 can be uniform or can become gradually steeper in the distal direction as shown in FIG. 22. During linear movement of the actuation member 816 along the translational axis TA from the first position to the second position, the proximal end 854 slidably engages the guiding surface 855 to follow the curvature of the guiding surface 855. As a result, the shells 830, 831 are rotated about the pin 824 away from one another in order to allow the prosthesis to move to the expanded configuration. Operation of the device 800 with movement of the shells and the cuffs to deploy a prosthesis to treat a body vessel can be gained with additional reference to FIGS. 9A-9E and FIGS. 10A-10C, as can be appreciated by one skilled in the art.

It can be appreciated by those skilled in the art that specific features of each embodiment of the deployment device are interchangeable among the device embodiments, even where no references to the specific features are made. For example, the device can include a feature of the previously described devices 10, 110, 410, 700 and/or 800. Further, a modification described with respect to a single device may be included with the other devices 10, 110, 410, 700 and/or 800 described herein.

The components of the devices described herein can be machined or molded from a biocompatible polymer or metal as can be appreciated by those skilled in the art. The actuation member can further comprise a driver, such as an electric motor coupled to a power source and/or controls for electronically controlling the speed, direction, and force of the actuation member. In one example, the actuation member is operable with a push of a button as can be appreciated by ones skilled in the art.

A concise description of prosthesis 15 will now be provided. One example of such prosthesis 15 is described in U.S. patent application Ser. No. 13/197,511, filed on Aug. 3, 2011, entitled "BLOOD PERFUSION DEVICE," which is incorporated herein by reference in its entirety. The prosthesis can include a generally tubular graft body and/or one or more anchoring members and/or supporting members together defining a fluid passageway. The prosthesis is movable between the radially compressed, delivery configuration and the radially expanded, deployed configuration. The prosthesis can be balloon expandable; however, it is preferred that the prosthesis is self-expandable. The anchoring members and/or supporting members can be attached to the graft body by sutures sewn therein, wire, staples, clips, bonding agents, or other methods that may be used to achieve a secure attachment to the graft body. The prosthesis has a size and shape suitable for at least partial placement within a body vessel, such as an artery or vein, and most particularly, for placement at the site of a vascular trauma. The prosthesis may be easily manipulated during delivery to a transected artery or vein during emergency surgery, and particularly, to obtain hemostasis while maintaining blood perfusion. The anchoring member and/or supporting member can be any stent pattern known to one skilled in the art. Examples of stent patterns is the Z-STENT® and ZILVER® stent, each available from Cook Medical Inc. (Bloomington, Ind.). The anchoring member and/or supporting member can be formed of a biocompatible metal, such as stainless steel (e.g., 316L SS), titanium, tantalum, nitinol or other shape memory materials, or a high-strength polymer. Preferably, anchoring devices can be included on at least the anchoring members to provide vessel fixation, while avoiding adverse conditions associated with disturbing the vasa vasorum and/or pressure induced necrosis of the medium muscular arteries of the type that may result from tying ligatures circumferentially around a connector or a vascular conduit. The anchoring devices can include various shaped member structures, including barbs, fibers, bristles, or outer protruding and penetrable media.

The graft body can be formed from conventional materials well known in the medical arts. The graft body may comprise an expanded polytetrafluoroethylene (ePTFE), polytetrafluoroethylene, silicone, polyurethane, polyamide (nylon), as well as other flexible biocompatible materials. The graft body can also be formed from known fabric graft materials such as woven polyester (e.g. DACRON®), polyetherurethanes such as THORALON® from Thoratec Corporation (Pleasanton, Calif.), polyethylene such as an ultra-high molecular weight polyethylene (UHMwPE), commercially available as DYNEEMA®. The graft body may also include a bioremodelable material, such as reconstituted or naturally-derived collagenous materials, extracellular matrix material (ECM), submucosa, renal capsule membrane, dermal collagen, dura mater, pericardium, fascia lata, serosa, peritoneum or basement membrane layers, intestinal submucosa, including small intestinal submucosa (SIS), stomach submucosa, urinary bladder submucosa, and uterine submucosa. One non-limiting example of a suitable remodelable material is the SURGISIS® BIODESIGN™, commercially available from Cook Medical Inc. (Bloomington, Ind.). Another suitable remodelable material is the graft prosthesis material described in U.S. Pat. No. 6,206,931 to Cook et al., which is incorporated herein by reference in its entirety.

Portions of the prosthesis can also include a coating of one or more therapeutic agents along a portion of the stent structure and/or the graft body. Therapeutic agents for use as biocompatible coatings are well known in the art. Non-limiting examples of suitable bio-active agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the vascular conduit by any suitable method that permits adequate retention of the agent material and the effectiveness thereof for its intended purpose. Although the device has been described in connection with its primary intended use for repair of vascular trauma, those skilled in the art will appreciate that the device may also be used to repair other traumatic conditions. Non-limiting examples of such conditions include aneurysms, such as abdominal aorta aneurysms, and surgery for tumor removal.

The axial length of the prosthesis 15 relative to the length of the prosthesis retaining chamber is such that ends of the prosthesis extend outwardly beyond the chamber. In this instance, the ends of the prosthesis may be expanded to a greater diameter than the radially compressed diameter of the prosthesis retained within the chamber. Preferably, such greater diameter of the ends of the prosthesis is less than the overall diameter of the vessel portion end opening. In one example, the prosthesis may be specially configured so that radial compression of a substantial intermediate portion of the prosthesis (e.g., at least about 80% L) to the first diameter, results in ends of the prosthesis (e.g., each up to about 10% L) having the greater diameter that is about 30% greater than the compressed configuration. To this end, the prosthesis is structured to expand up to about 3% in diameter or less for every 1% of exposed length.

Drawings in the figures illustrating various embodiments are not necessarily to scale. Some drawings may have certain details magnified for emphasis, and any different numbers or proportions of parts should not be read as limiting, unless designated as such in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. It should be understood that the following claims, including all equivalents, are intended to define the spirit and scope of this invention.

We claim:

1. A method of treating a body vessel, comprising:
introducing a deployment device having a prosthesis within a body through a trauma pathway having a first opening of a first vessel portion and a second opening of a second vessel portion, the first and second openings being exposed to the trauma pathway and spaced apart from each other, the device comprising a support frame and an actuation member coupled to the support frame, the actuation member movable relative to the support frame between a first position and a second position, a retaining member coupled to the support frame, the retaining member movable between a closed position and an open position, wherein when in the closed position the retaining member forms a retaining chamber to retain at least an intermediate length of the prosthesis in a radially compressed configuration, wherein the actuation member is in the first position and the retaining member is in the closed position;

introducing a first outer end of the prosthesis into the first opening of the first vessel portion of a body vessel;

introducing a second outer end of the prosthesis into the second opening of the second vessel portion of the body vessel; and moving the actuation member from the first position to the second position, whereby the retaining member moves to the open position from the closed position to allow the prosthesis to move to a radially expanded configuration, wherein the retaining member is biased towards the closed position.

2. The method of claim 1, wherein the retaining member further comprises a first shell and a second shell, wherein when the retaining member is in the closed position the first shell and the second shell are positioned in close proximity to form the retaining chamber, and in the open position, the first shell and the second shell are rotated away from one another to allow the prosthesis to move to the radially expanded configuration.

3. The method of claim 1, wherein the device further comprises a retractable end to selectively retain an outer end of the prosthesis in the radially compressed configuration, the method further comprising moving the retractable end to a position to permit expansion of the outer end of the prosthesis prior to the moving the actuation member step.

4. The method of claim 1, wherein the prosthesis extends between the first outer end and the second outer end along a longitudinal axis, and the support frame extends along a translational axis, wherein the translational axis is angularly offset from the longitudinal axis.

5. The method of claim 4, wherein movement of the actuation member from the first position to the second position is along the translational axis.

6. The method of claim 1, wherein the retaining member in the closed position extends only along the intermediate length of the prosthesis such that the first outer end and the second outer end are exposed.

7. The method of claim 1, wherein the first vessel portion of the body vessel is a non-blood supplying end of the body vessel.

8. A method of treating a body vessel, comprising:

introducing a deployment device having a prosthesis within a body, the prosthesis extending between a first outer end and a second outer end along a longitudinal axis, and the device comprising a support frame and an actuation member coupled to the support frame, the support frame extending outwardly from the prosthesis along a translational axis which is angularly offset from the longitudinal axis, the actuation member movable relative to the support frame between a first position and a second position, a retaining member coupled to the support frame, the retaining member movable between a closed position and an open position, wherein when in the closed position the retaining member forms a retaining chamber to retain at least an intermediate length of the prosthesis in a radially compressed configuration, wherein the actuation member is in the first position and the retaining member is in the closed position;

introducing the first outer end of the prosthesis into a first vessel portion of a body vessel;

introducing the second outer end of the prosthesis into a second vessel portion of the body vessel; and moving the actuation member from the first position to the second position, whereby the retaining member moves to the open position from the closed position to allow the prosthesis to move to a radially expanded configuration, wherein the actuation member is moved along the translational axis from the first position to the second position.

9. The method of claim 8, further comprising preloading the prosthesis into the retaining member prior to introducing the deployment device within the body.

10. The method of claim 8, further comprising clamping the first vessel portion and the second vessel portion prior to introducing the deployment device within the body.

11. The method of claim 8, further comprising opening a pathway to the body vessel.

12. The method of claim 11, further comprising opening the pathway by transecting the pathway.

13. The method of claim 11, further comprising suturing the first vessel portion and the second vessel portion to maintain the pathway to the body vessel.

14. The method of claim 8, further comprising pulling the first vessel portion over the first outer end of the prosthesis after introducing the first outer end of the prosthesis into the first vessel portion.

15. A method of treating a body vessel, comprising:

introducing a deployment device having a prosthesis within a body, the device comprising a support frame and a first operable member coupled to the support frame, and a second operable member coupled to the support frame, the first and second operable members each being movable relative to the support frame between a first position and a second position, a retaining member coupled to the support frame, the retaining member movable between a closed position and an open position, wherein when in the closed position the retaining member forms a retaining chamber to retain at least an intermediate length of the prosthesis in a radially compressed configuration, and a retractable cuff coupled to the second operable member and movable between a delivery configuration and a deployed configuration, wherein, in the delivery configuration, the cuff is fitted over one of a first outer end and a second outer end of the prosthesis, wherein the first operable member is in the first position, the second operable member is in the first position, the retractable cuff is in the delivery configuration, and the retaining member is in the closed position;

introducing the first outer end of the prosthesis into a first vessel portion of a body vessel;

introducing the second outer end of the prosthesis into a second vessel portion of the body vessel;

moving the second operable member from the first position to the second position, whereby the retractable cuff moves to the deployed configuration and the retractable cuff is removed from the one of the first outer end and second outer end of the prosthesis to allow for expansion thereof; and moving the first operable member from the first position to the second position, whereby the retaining member moves to the open position from the closed position to allow the prosthesis to move to a radially expanded configuration.

16. The method of claim 15, wherein movement of the retractable cuff is locked after the retractable cuff is moved to deployed configuration.

17. The method of claim 15, wherein the deployment device comprises a first retractable cuff on the first outer end and a second retractable cuff on the second outer end of the prosthesis, wherein the second operable member is coupled to at least the first retractable cuff.

18. The method of claim 17, further comprising moving a third operable member from the first position to the second position, whereby the second retractable cuff moves to the deployed configuration and the second retractable cuff is removed from the second outer end of the prosthesis to allow for expansion thereof.

\* \* \* \* \*